(12) United States Patent
Shiratori et al.

(10) Patent No.: US 7,028,547 B2
(45) Date of Patent: Apr. 18, 2006

(54) BODY MOTION DETECTOR

(75) Inventors: Norihiko Shiratori, Nagano-ken (JP); Kazutoyo Ichikawa, Nagano-ken (JP); Hideki Tamura, Nagano-ken (JP); Yuji Izawa, Nagano-ken (JP); Masaki Terashima, Nagano-ken (JP)

(73) Assignee: MicroStone Co., Ltd., Nagano-ken (JP)

( * ) Notice: Subject to any disclaimer, the term of this patent is extended or adjusted under 35 U.S.C. 154(b) by 0 days.

(21) Appl. No.: 10/468,850

(22) PCT Filed: Mar. 5, 2002

(86) PCT No.: PCT/JP02/01998

§ 371 (c)(1),
(2), (4) Date: Sep. 25, 2003

(87) PCT Pub. No.: WO02/069803

PCT Pub. Date: Sep. 12, 2002

(65) Prior Publication Data

US 2004/0094613 A1    May 20, 2004

(30) Foreign Application Priority Data

| Mar. 6, 2001 | (JP) | ............... 2001-110616 |
| Jun. 27, 2001 | (JP) | ............... 2001-232847 |
| Sep. 26, 2001 | (JP) | ............... 2001-333496 |
| Nov. 28, 2001 | (JP) | ............... 2001-402169 |

(51) Int. Cl.
*G01P 15/00* (2006.01)
*G01P 7/00* (2006.01)

(52) U.S. Cl. ............. 73/495; 702/141; 702/189; 702/142

(58) Field of Classification Search ............ 73/489, 73/492, 493, 494, 495, 498, 499; 702/141, 702/142, 189
See application file for complete search history.

(56) References Cited

U.S. PATENT DOCUMENTS 4,699,379 A * 10/1987 Chateau et al. ............. 473/59
5,694,340 A * 12/1997 Kim ..................... 702/141
6,046,531 A    4/2000 Gouji et al.

(Continued)

FOREIGN PATENT DOCUMENTS

CN    1072791    6/1993
EP    0666544    * 8/1995

(Continued)

*Primary Examiner*—Helen Kwok
(74) *Attorney, Agent, or Firm*—Dennison, Schultz, Dougherty & MacDonald

(57) ABSTRACT

A movement detecting device comprises a container (10), at least a first vibrator (16) which vibrates in accordance with a physical movement in a first direction (X), and a second vibrator (17) which vibrates about a second direction (Z), the first and second vibrators mounted in the container. The vibrations of the first and second vibrators are converted into an electric signal, and a value of the converted signal is shown on a display.

10 Claims, 26 Drawing Sheets

U.S. PATENT DOCUMENTS

| | | | |
|---|---|---|---|
| 6,048,324 A * | 4/2000 | Socci et al. | 600/595 |
| 6,059,576 A * | 5/2000 | Brann | 434/247 |
| 6,183,365 B1 * | 2/2001 | Tonomura et al. | 463/36 |
| 6,183,425 B1 * | 2/2001 | Whalen et al. | 600/592 |
| 6,227,048 B1 | 5/2001 | Kikuchi et al. | |
| 6,433,690 B1 * | 8/2002 | Petelenz et al. | 340/573.1 |
| 6,487,992 B1 * | 12/2002 | Hollis | 119/712 |
| 6,571,193 B1 * | 5/2003 | Unuma et al. | 702/141 |
| 6,585,622 B1 * | 7/2003 | Shum et al. | 482/8 |
| 6,834,436 B1 * | 12/2004 | Townsend et al. | 33/512 |

FOREIGN PATENT DOCUMENTS

| | | |
|---|---|---|
| JP | 4/18324 | 2/1992 |
| JP | 10-113343 | 5/1998 |
| JP | 10/113343 | 5/1998 |
| JP | 11-290557 | * 10/1999 |
| JP | 11/325917 | 11/1999 |
| JP | 2000/206141 | 7/2000 |
| JP | 2000-206141 | 7/2000 |

* cited by examiner

SET DISTANCE FROM TOKYO

≪ FORWARD | REVERSE ≫ | NEW

CITY NAME: CITY ①

PREFECTURE COUNTRY: PREF ①

DISTANCE: 50.0 km

MESSAGE STORE

REGISTER | ALTER | DELETE

END

BODY MOTION DETECTOR

TECHNICAL FIELD

The present invention relates to a device for detecting physical movements.

BACKGROUND ART

There are proposed various inventions relating to such a device. The device is worn on a body of a user to detect physical movements of the body by a sensor and the movement condition is determined based on the detected data so as to be used for health control and other objectives. For example:

(1) Japanese Patent Application Laid-Open 10-295651 discloses a technique wherein a mobile terminal having an acceleration sensor is worn on a waist of a user. Personal data stored beforehand and the quantity of movement which is automatically measured are transmitted to an external central computer by telephone line and analyzed for health check, and the result is transmitted to the movable terminal and displayed as required by the user.

(2) Japanese Patent Application Laid-Open 2000-41953 discloses a technique where a movement data collecting device has a physical movement sensor for detecting movements and is worn on a body of a user. The detected data undergoes a primary process and are transmitted to an external personal computer. A movement data output device provided in the computer carries out a secondary process based on personal information and the processed data is transmitted. The device renders it unnecessary to accumulate the personal information and the large size secondarily processed information therein so as to improve the operability and reduce the memory capacity thereof.

(3) In Japanese Patent Application Laid-Open 2000-41952, in order to reduce the memory capacity of a movement information detecting device, a built-in MPU calculates step count, walking pace, the type of movement, strength of the exercise, consumed calorie and other bodily information based on the output of a sensor and a movement detecting circuit, and stores, displays or externally transmits the calculated result every minute.

The devices in the above described conventional inventions (1), (2) and (3) are not small enough and are therefore often burdens to users.

An object of the present invention is to provide a small and a lightweight device which will be less burdensome to the user when worn.

DISCLOSURE OF THE INVENTION

According to the present invention, there is provided a movement detecting device comprising a container, at least a first vibrator which vibrates in accordance with a physical movement in a first direction, and a second vibrator which vibrates about a second direction, the first and second vibrators being mounted in the container, a converting means for converting the vibrations of the first and second vibrators into at least one electric signal, a display for indicating a value of the converted signal.

The first vibrator comprises a pair of parallel vibrating rods, and the second vibrator comprises a tuning fork.

The converting means comprises an elastic plate made of a piezoelectric material and detector electrode films attached to the vibrators.

The container is housed in a case and the case is adapted to be worn on a wrist.

The first vibrator detects an acceleration and the second vibrator detects an angular velocity.

The first direction is a vertical direction the second direction is a direction within a vertical plane.

The present invention further provides a movement detecting device comprising a piezoelectric plate supported on a supporter, a plurality of electrode films disposed and adhered in three radial directions on the piezoelectric plate, a mass loading element attached on the underside of a center of the piezoelectric plate, and a display for indicating outputs of the electrode films.

The tuning fork comprises a pair of outer prongs and a middle prong between the outer prongs.

The tuning fork is disposed at a center and the vibrating rods are disposed at both sides of the tuning fork in parallel to the fork in longitudinal direction thereof.

Each of the vibrating rods has a base, a fixing portion thereof is secured to the container and an end portion is attached to the container by way of a fixing portion smaller in area than the fixing portion at the base.

BRIEF DESCRIPTION OF DRAWINGS

FIGS. 4b and 4c are flowcharts describing the operations where energy is calculated in the flowchart of FIG. 4a;

FIG. 32 shows a goal setting screen of the external device;

FIG. 34 is an example of a setting screen for rendering the device to represent the attained distance by a specific location names during the step count calculating process.

BEST MODE FOR EMBODYING THE INVENTION

Figure 1:
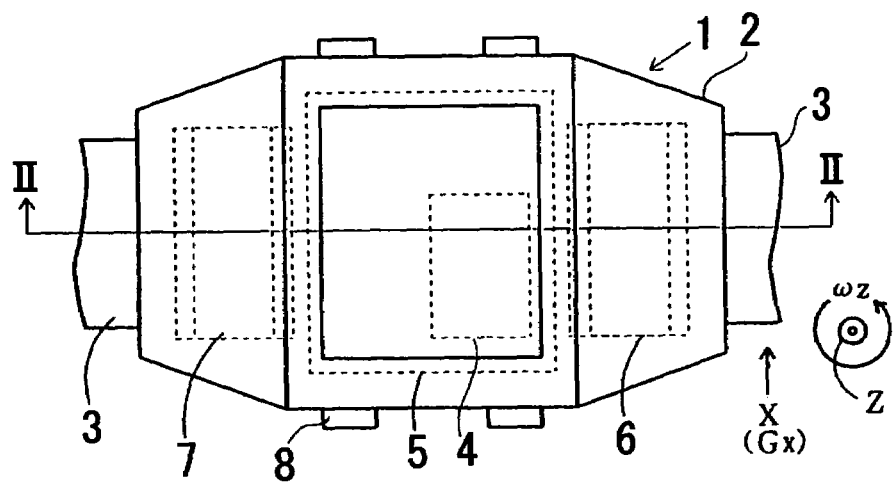
FIG. 1 is a plan view of a movement measuring device.
Figure 2:
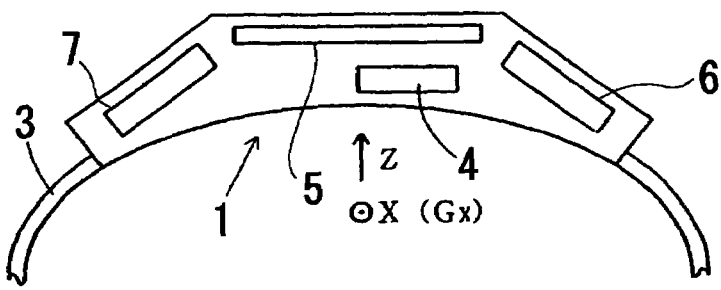
FIG. 2 is a sectional view taken along a line II—II of FIG. 1.

A first embodiment of a physical movement detecting and analyzing device according to the present invention will now be described. FIG. 1 is a plan view of a movement measuring device, and FIG. 2 is a sectional view taken along a line II—II of FIG. 1. A movement measuring device 1 comprises a case 2 having a shape of a watch and which can be worn on a wrist of a user by a pair of bands 3 wrapped around the wrist. The case 2 is provided with a movement sensor 4, liquid crystal display 5, transmission circuit module 6 for external communication, power supply battery 7, and manipulating switches 8. The movement measuring device 1 is rendered thin and small so as not to burden the user. The display 5 is disposed on the largest surface of the device so as to be easily viewed. The movement sensor 4 is disposed in parallel to the display 5. The display 5 which is a liquid crystal display panel is small in thickness and the movement sensor 4 is contained in a thin package.

The movement sensor 4 is adapted to measure acceleration and angular velocity in at least one direction with respect to a certain direction of the movement measuring device 1. An acceleration Gx shown in the drawing corresponds to that of a vertical direction of the body, namely the perpendicular direction (hereinafter referred to as an X-axis) when the user standing up naturally lets his arm fall along the body. The direction of a measured angular velocity ωz corresponds to the natural rotating direction of the lower arm about the right-to-left axis (Z-axis) of the body when the arm is rotated in parallel to the side of the body.

The reason why the movement sensor 4 is disposed in parallel to the display 5 is explained hereinafter. Provided that the movement measuring device 1 is worn like a watch so that the display surface is disposed at the back side or the palm side of the wrist, when the body is upright and the upper arm is bent and stretched at the elbow or the upper arm is rotated about the shoulder, the rotating surface becomes parallel to the side of the body and hence to the display surface of the measuring device 1 worn on the wrist like a watch, that is the display 5. Thus, it is preferable to dispose the movement sensor 4 in parallel to the display 5 so that an angular velocity sensor provided within the sensor 4 has a rotation detecting surface thereof parallel to the largest surface of the device.

Figure 3:
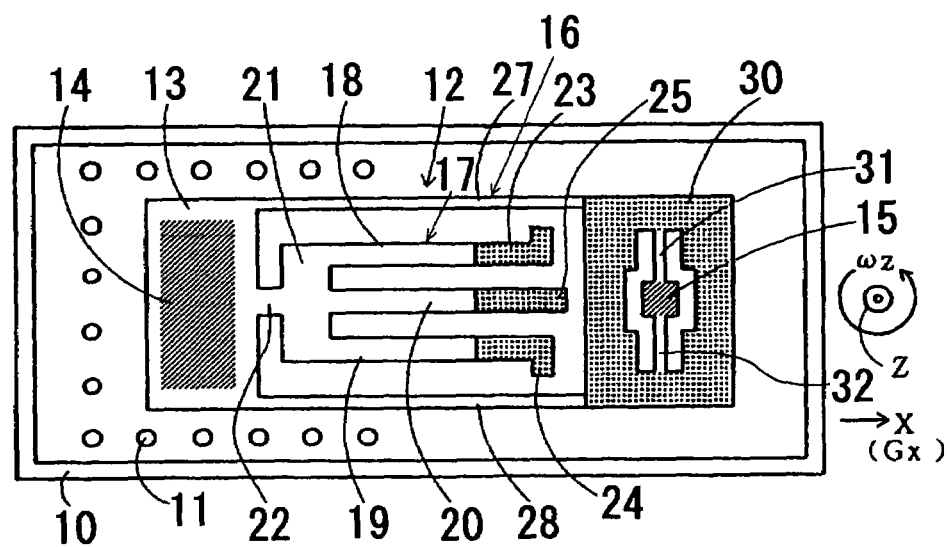
FIG. 3 is a plan view showing an example of a movement sensor in a first embodiment of the present invention.

FIG. 3 is a plan view showing an example of a movement sensor provided in the first embodiment of the present invention. The construction of the movement sensor is adapted to conform to all of the requirements described above with regard to the shape, disposition and the detecting direction. A container 10, which has a shape of a shallow box and is air-tight, is shown with the ceiling thereof taken off so that the inner construction is visible. A plurality of hermetic terminal pins 11 which pass through the bottom of the container is provided in the container. Each pin is connected to one of a group of detecting electrode films (not shown) provided on a movement sensor vibrator 12 by a bonding wire. The movement sensor vibrator 12 is cut out from a piece of piezoelectric material by the photolithography technique so as to integrally form an acceleration sensor portion 16 and an angular velocity sensor portion 17. The underside of a fixing portion 14 and the underside of a fixing portion 15 having a smaller area, formed on a substrate 13 of the movement sensor vibrator 12, are adhered on a pedestal (not shown) of the container so as to be supported thereon.

The angular velocity sensor portion 17 is a portion having a shape of a so-called three-pronged tuning fork comprising first outer prong 18, second outer prong 19, middle prong 20, each formed in a shape of an L, fork base 21, and a fulcrum 22. As in the ordinary two-pronged tuning fork, each of the outer prongs 18 and 19 is cantilevered so as to vibrate in symmetry with respect to the symmetry axis at a predetermined frequency dependent on a vibrating current from an oscillating circuit provided in a angular velocity measuring circuit (not shown). Although the middle prong 20 does not vibrate, a detecting electrode (not shown) is attached to each of the four surfaces of the middle prong so as to detect the deflections thereof. Additional mass elements 23, 24, 25 are formed by thick metal plating layers on the tip ends of the respective prongs so that the natural frequencies are decreased and equalized to those of other prongs. Alternatively, the natural frequency of the middle prong 20 may be adapted to differ from those of the outer prongs as appropriate.

When the movement sensor vibrator 12 is rotated at an angular velocity ωz in the direction shown in the figure, that is, about a rotational axis parallel to a Z-axis which is perpendicular to the face of the paper, a Coriolis force proportional to the angular velocity is generated at both of the outer vibrating prongs 18 and 19. The direction of the Coriolis force is in the longitudinal direction of the prongs, and if a force oriented toward the tip end is applied to the prong 18 at a certain instant, a force oriented toward the base of the prong 19 is applied. The directions of the forces change in a sine curve and are periodically inverted in synchronism with the vibrations of the prongs. Since the outer prongs are disposed apart from each other in parallel to each other, and the eccentric directions of the additional mass elements oppose each other with respect to the axis of the prongs, the two forces constitute a couple of forces, so that the fork base 21 sways, thereby generating very small rotational vibrations about the fulcrum 22. The middle prong 20, sensing the vibration of the fork base 21 caused by a moment generated by the Coriolis force, vibrates at an amplitude which is in proportion to the Coriolis force. A vibration voltage extracted from the detecting electrode provided on the middle prong 20 is a detected signal representing the angular velocity $\omega z$ which is then converted into a display signal and shown on the display 5.

The acceleration sensor potion 16 of the movement sensor vibrator 12 comprises a pair of vibrating rods 27 and 28, each of which is supported at an end thereof and which vibrates in parallel to each other, and an additional mass element 30. The mass of the additional mass element 30 is a sum of a mass of a large portion of the material forming the base and a mass of the thick plating formed on the surface thereof. The additional mass element 30 comprises a pair of supporting springs 31 and 32 disposed apart from each other, thereby forming two blank spaces. Together with the fixing portion 15, the supporting springs support the additional mass element 30 so as to allow the mass element to be slightly displaced in an X-direction shown in the drawing. The fixing portion 15 holds the additional mass element 30 to prevent the excessive displacement thereof in Y- and Z-directions, but allows a slight displacement in the X-direction. The vibrating rods 27 and 28, the ends of which are fixed, are each vibrated by an oscillating circuit in a vibrating posture which is an arch symmetric to that of the other with respect to the symmetry axis of the movement sensor vibrator 12.

Although the oscillating frequency is normally constant, when an acceleration Gx in the X-direction shown in the figure is exerted on the additional mass element 30, the vibrating rods 27 and 28 are compressed or expanded in the longitudinal direction, so that the oscillating frequency is increased or decreased and hence changed. Accordingly, a reference frequency is set so as to be compared with the changing frequency, so that the changing direction and the amount of the change is detected at the detecting electrodes provided on the vibrating rods 27 and 28, thereby enabling to detect the acceleration Gx in the direction of the X-axis. The oscillating frequencies of the outer prongs 18 and 19, which are the vibrators for the angular velocity sensor, may be used instead.

The outputs, namely the measured acceleration Gx and angular velocity $\omega z$ are processed in various manner so as to be used for determining the type of movements and calculating energy consumption. The final information is immediately shown on the display 5 on the wrist for the user to monitor. Additionally, the data before, during and after the calculation are transmitted to a stationary computer through wireless, or daily data through a cable so that the final information may be visualized or recorded based on the calculation at the computer.

One of the features of the present invention lies in the algorism for obtaining required information from the acceleration Gx and the angular velocity $\omega z$. An outline of the algorism is described and the operation thereof is explained in detail with reference to a flowchart hereinafter.

The measured values of acceleration Gx and angular velocity $\omega z$ are data sampled at 10 to 100 Hz, for example at 20 and 50 Hz. Moreover, as the amount representing the levels of the acceleration Gx and angular velocity $\omega z$, a sum of the absolute values or a sum of the power of the absolute values of predetermined numbers of the sampled data are used.

(1) Identifying physical action: If there is a certain degree of periodicity in the sampling data of the acceleration Gx and angular velocity $\omega z$, it is determined that the physical movement is either walking or running. If not, the movement is other exercises. In addition, the walking and running can be discriminated from each other by the difference in the acceleration Gx. These movements can be further classified into several intensity levels by the amount representing the levels of the acceleration Gx and angular velocity $\omega z$. Moreover, the number of steps is used when there is a periodicity in order to determine walking or running.

(2) Short-term energy consumption: Energy consumption for various types of movement per unit weight (kg) is given as shown in Table 1 as a "coefficient per movement" based on those of a male of 20 to 29 years of age (from Sports Science Committee of Japan Amateur Sports Association). Additionally, correction coefficients for other age groups and sex are given as shown in Table 2. Accordingly, when the type of the movement is determined, the energy consumption can also be calculated.

TABLE 1

COEFFICIENT PER MOVEMENT
(unit: kcal/kg/minute)

| Sit-up movement | | Standing movement | |
|---|---|---|---|
| Having a meal | 0.0269 | Stroll | 0.0464 |
| Desk work | 0.0304 | Walking (normal) | 0.057 |
| Driving a car | 0.0287 | Climbing stairs | 0.1349 |
| Rest or chat | 0.0233 | Descending stairs | 0.0658 |
| Sewing | 0.0287 | Cooking | 0.0481 |
| Hobby and entertainment | 0.0287 | Using vacuum cleaner | 0.0499 |
| Cultural activities | 0.0233 | Using washing machine | 0.041 |
| Ironing | 0.0464 | Drying laundry | 0.0587 |

| Walking | | Exercise | |
|---|---|---|---|
| 60 m/min | 0.0534 | Ping pong exercise | 0.149 |
| 70 m/min | 0.0623 | Rhythmic exercise | 0.1472 |
| 80 m/min | 0.0747 | Gymnastics (light) | 0.0552 |
| 90 m/min | 0.0906 | Gymnastics (heavy) | 0.0906 |
| 100 m/min | 0.1083 | | |

| Bicycling | | Jogging | |
|---|---|---|---|
| Normal | 0.0658 | Light | 0.1384 |
| Level ground 10 km/hr | 0.08 | Heavy | 0.1561 |
| Uphill 10 km/hr | 0.1472 | | |
| Downhill | 0.0269 | | |

TABLE 2

CORRECTING COEFFICIENT BASED ON AGE AND SEX

| Age | Male | Female |
|---|---|---|
| 10 | 1.542 | 1.471 |
| 11 | 1.454 | 1.371 |
| 12 | 1.375 | 1.288 |
| 13 | 1.288 | 1.213 |
| 14 | 1.217 | 1.142 |
| 15 | 1.158 | 1.079 |
| 16 | 1.125 | 1.038 |
| 17 | 1.096 | 1.008 |

TABLE 2-continued

CORRECTING COEFFICIENT BASED ON AGE AND SEX

| Age | Male | Female |
| --- | --- | --- |
| 18 | 1.071 | 1.004 |
| 19 | 1.05 | 0.999 |
| 20~29 | 1 | 0.971 |
| 30~39 | 0.954 | 0.917 |
| 40~49 | 0.925 | 0.879 |
| 50~59 | 0.917 | 0.863 |
| 60~64 | 0.908 | 0.858 |
| 65~69 | 0.9 | 0.863 |
| 70~74 | 0.896 | 0.863 |
| 75~79 | 0.875 | 0.871 |
| 80~ | 0.867 | 0.867 |

(3) Long-term energy consumption: A long-term energy consumption can be obtained by integrating the short-term energy consumption which changes in accordance with time. Alternatively, the movement sensor can be operated intermittently instead of constantly. In such a case, when the type and the strength of a movement is determined dependent on the data obtained while in motion, the calculated energy consumption is added up assuming that the same movement has continued during the interval between the intermittent operation, for example for several to ten odd minutes.

Figure 4A:
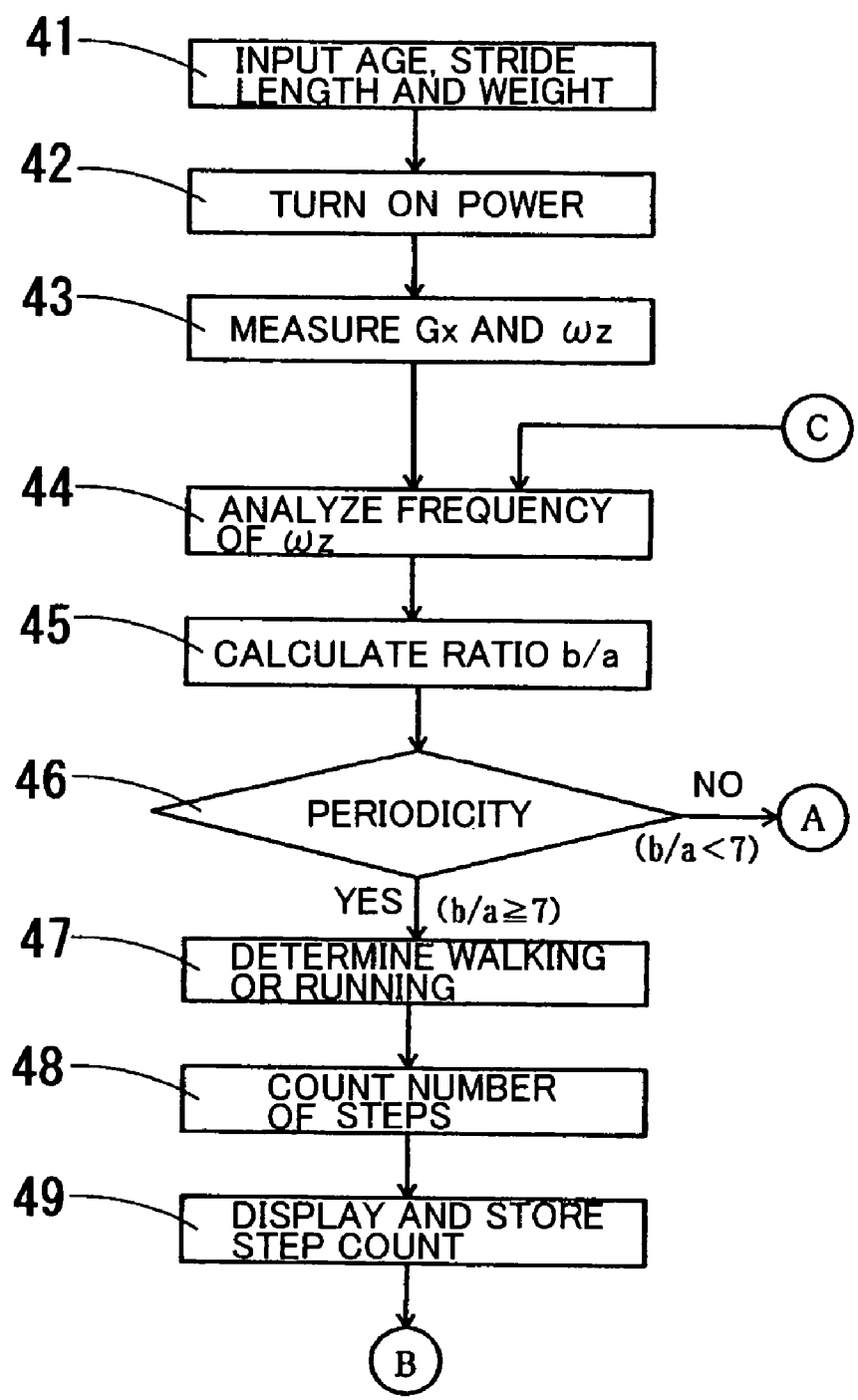
FIG. 4a is a flowchart describing the operation of the first embodiment of the movement measuring device of the present invention.
Figure 4B:
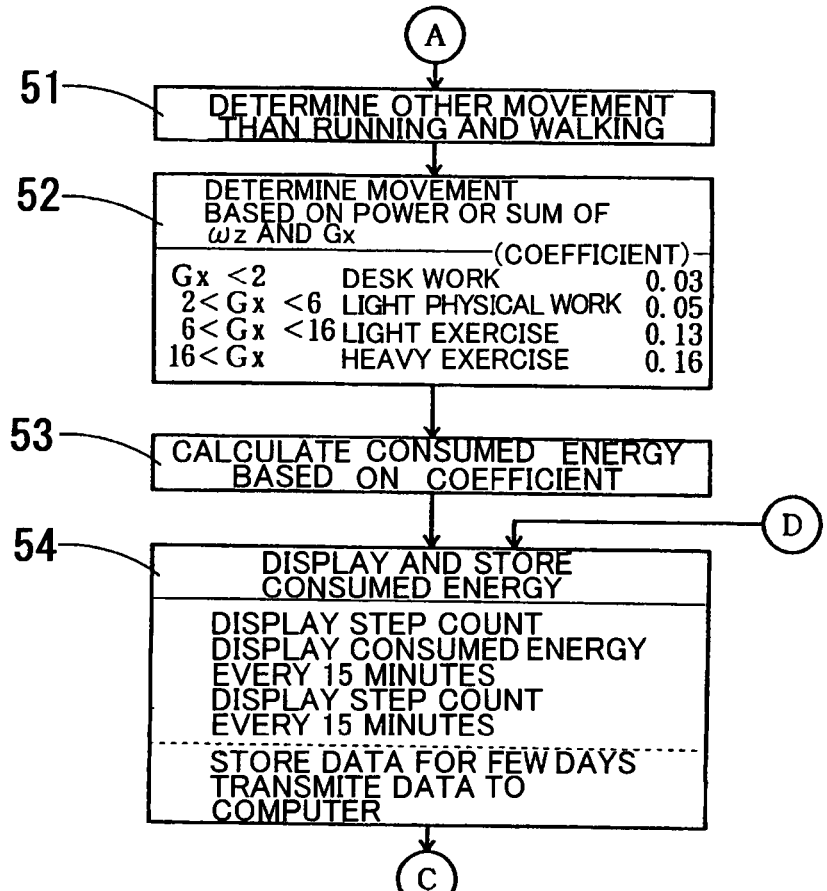
Figure 4C:
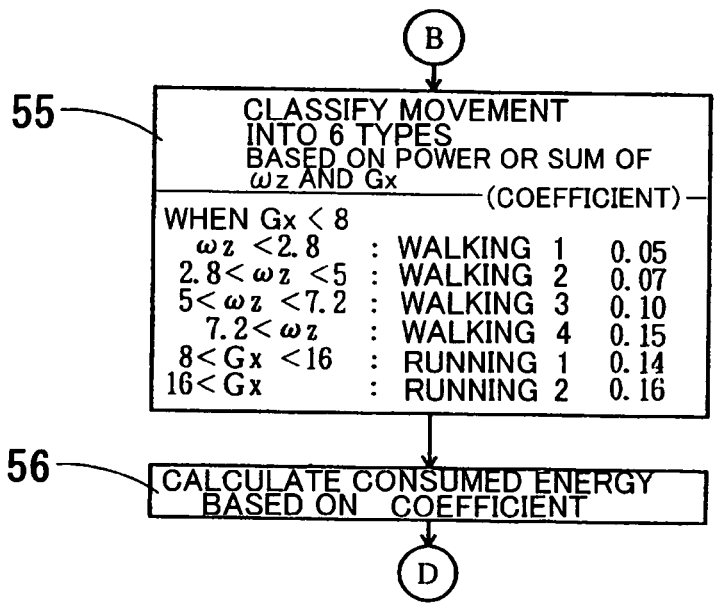

FIG. 4a is a flowchart describing the operation of the first embodiment of the movement measuring device of the present invention and FIGS. 4b and 4c are flowcharts describing the operations where energy is calculated in the flowchart of FIG. 4a.

Referring to FIG. 4a, at a step 41, data regarding age, sex, weight, and in accordance with the object, data such as a stride length of the user are input. At a step 42, the power is turned on so that the movement sensor and the measuring circuit start the operation. The acceleration Gx and angular velocity $\omega z$ are measured a number of times at a predetermined timing at a step 43. At a step 44, the angular velocity $\omega z$ is sampled at 20 Hz, for example, and the frequency analysis is carried out by dispersed Fourier transform every 0.1 Hz to determine whether there is a frequency lower than 4 Hz. The data is updated every two seconds. The frequency at walking is about 0.5 to 1.8 Hz. At a step 45, a ratio between an average a of the Gx data during the period and a peak value b is calculated.

At a step 47, a periodicity is determined. When the ratio b/a is smaller than 7, (b/a<7), it is determined that a periodicity does not exist and the program proceeds to a junction A to calculate the consumed energy for a non-periodic movement. When the ratio b/a is larger than 7 (b/a≧7), it is determined that the user is either walking or running. A peak frequency of the angular velocity $\omega z$ is multiplied by two and then doubled for a two-second period to obtain the number of steps taken during the two-second period at a step 48. The ratio b/a of 7 used as a criterion for determining the types of the movement is selected based on experiments and is a value most deemed appropriate when the sum of absolute values is used as the data. At a step 49, the step count is displayed, and the count corresponding up to the maximum of 24 hours, for example, and the variation thereof ranging several days are stored. The program then proceeds to a starting point B of the flow for calculating the consumed energy during walking or running.

Referring to FIG. 4b, in the case where it is determined at the step 46 that the movement is not periodic, it is determined at a step 51 that the movement is other movements besides walking or running. At a step 52, the non-periodic movements are categorized using a power or a sum of absolute values of acceleration Gx for two seconds which is sampled at 20 Hz. Thus a movement coefficient is determined as shown in the drawing. Namely, when acceleration Gx is smaller than 2 (Gx<2), the movement is a desk work. When 2<Gx<6, the movement is determined as a light physical work, when 6<Gx<16, a light exercise, and 16<Gx, a hard exercise. A predetermined movement coefficient is applied for each of the categorized movement. Meanwhile, values representing the levels of the acceleration Gx and angular velocity $\omega z$ used herein are output voltage values of the measuring circuit, and therefore, although in proportion to the acceleration and angular velocity and the absolute values thereof, they are not values having dynamic units.

At a step 53, consumed energy is calculated in accordance with the following equation.

consumed energy [kcal]=movement coefficient [kcal/kg/min]×weight [kg]×time [minute]×correcting coefficient At a step 54, the consumed energy is shown and stored, and in addition, the data are transferred through a wireless or a cable to the external computer as required. It is appropriate to display the consumed energy every 15 minutes, or a daily value, for example. When the data processing is completed, the program returns from an end C to the step 44 of FIG. 4a for the next movement analysis.

When the movement is walking or running, the program goes from the step 49 to a step 55 in FIG. 4c where the movement is further classified to determine the movement coefficient thereof. Namely, using each of powers of the acceleration Gx and angular velocity $\omega z$, or a sum of the absolute value thereof, when Gx<8 and at the same time, $\omega z$<2.8, the movement is determined as Walking 1, when 2.8<$\omega z$<5, as Walking 2, 5<$\omega z$<7.2, as Walking 3, 7.2<$\omega z$, as Walking 4, 8<Gx<16, as Running 1, and 16<Gx, as Running 2. At a step 56, the consumed energy is calculated using the movement coefficient in accordance with the aforementioned equation. Thereafter, the program goes to the step 54 of FIG. 4b through the junction D so as to display and store the data.

The usability of the present invention is hereinafter examined with reference to FIGS. 5 to 13 showing results of experiments using the algorism of the present invention.

Figure 5:
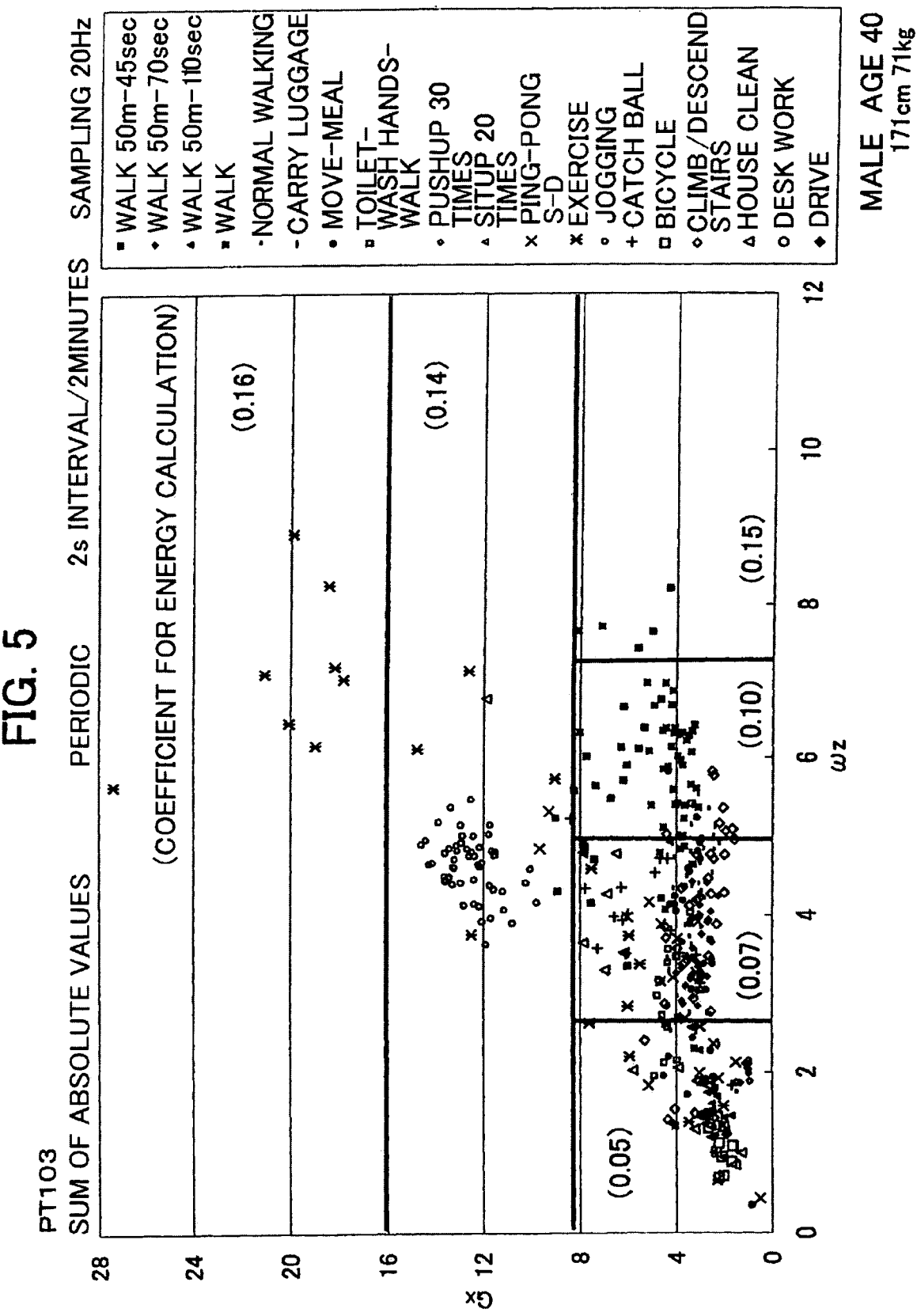
FIG. 5 is a graph showing a relationship between sum of absolute values of acceleration Gx and absolute values of angular velocity ωz in the movement conducted by a first subject and determined as having a periodicity.
Figure 6:
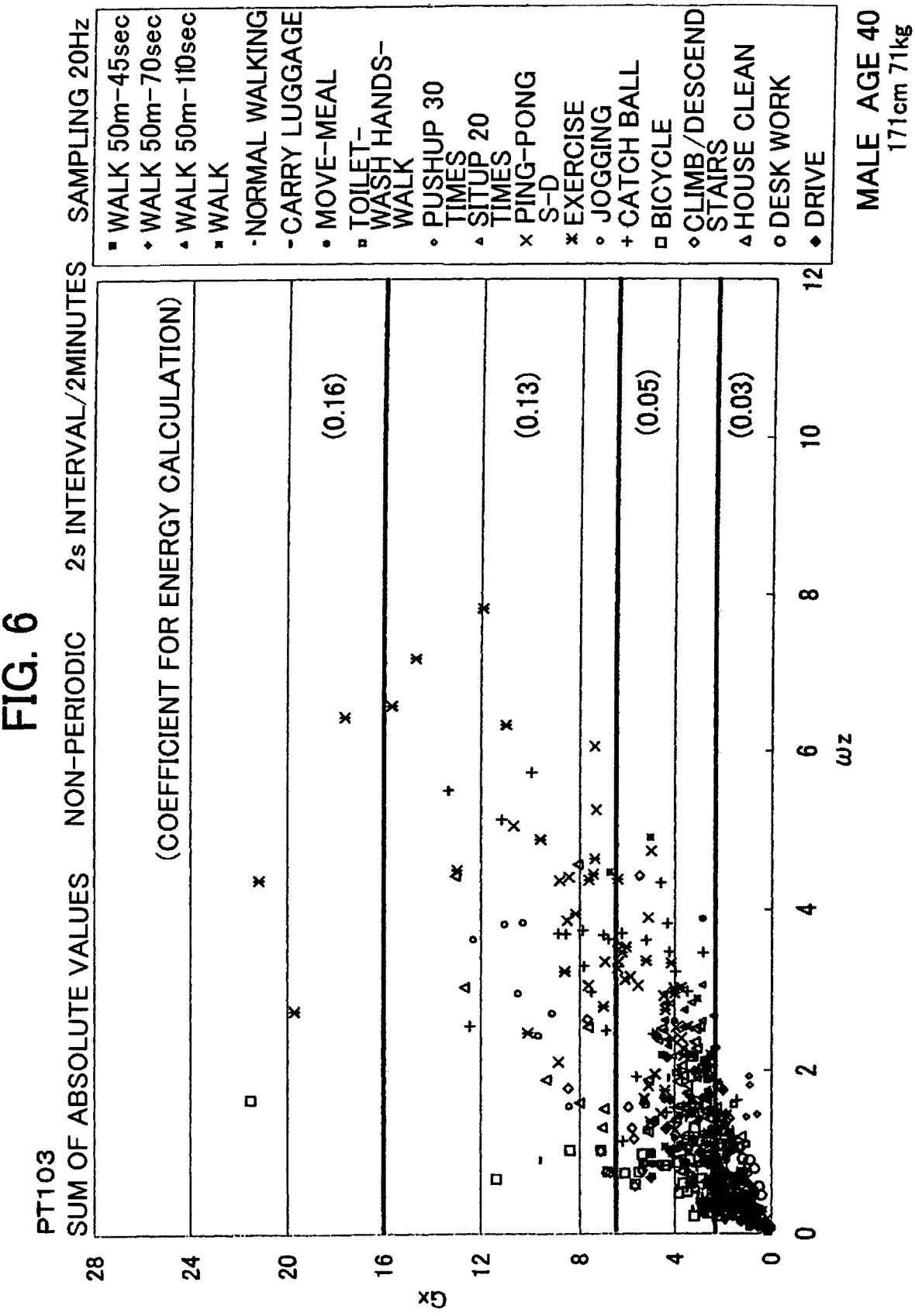
FIG. 6 is a graph showing a relationship between sum of absolute values of acceleration Gx and absolute values of angular velocity ωz in the movement by the same subject and determined as having no periodicity.

FIG. 5 is a graph showing a relationship between sum of absolute values of acceleration Gx and that of angular velocity $\omega z$ in the movement by a subject P determined as having a periodicity, and FIG. 6 is a graph showing a relationship between sum of absolute values of acceleration Gx and that of angular velocity $\omega z$ in the movement by the same subject P determined as having no periodicity. From these graphs, the intensities of the running and heavy exercise can be classified using the acceleration Gx, and the intensities of walking and other movements can be classified using the angular velocity $\omega z$.

Figure 7:
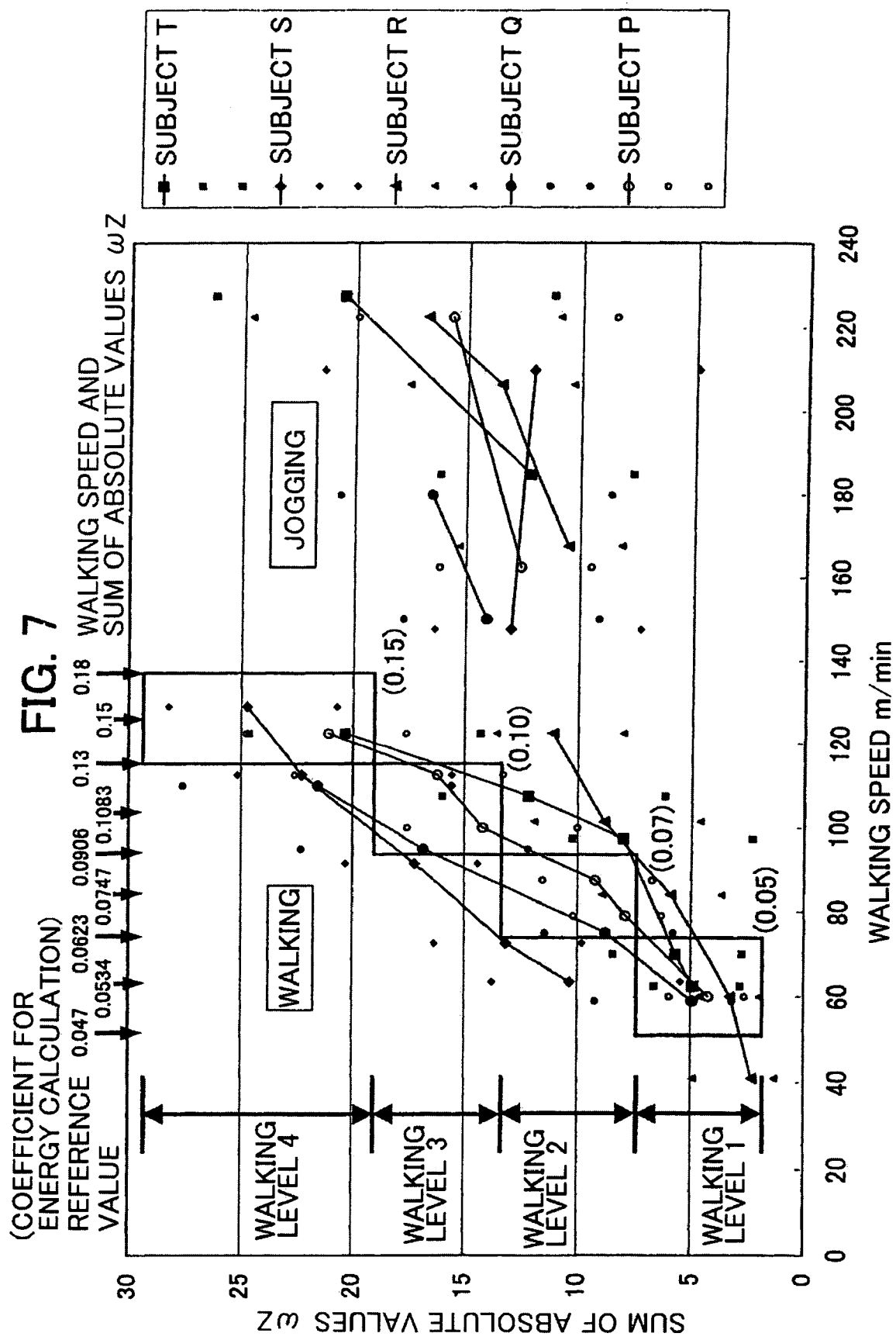
FIG. 7 is a graph showing a relationship between speed of walking and running and sum of absolute values of the angular velocity ωz conducted by five subjects.

FIG. 7 is a graph showing a relationship between speed of walking and running and sum of absolute values of the angular velocity $\omega z$ of five subjects P, Q, R, S and T. The speed of walking is in proportion to the angular velocity $\omega z$, so that it is possible to estimate the walking speed, that is the intensity, from the angular velocity $\omega z$. On the other hand, it is difficult to estimate the running speed from the angular velocity $\omega z$ since the elbows are bent during running.

Figure 8:
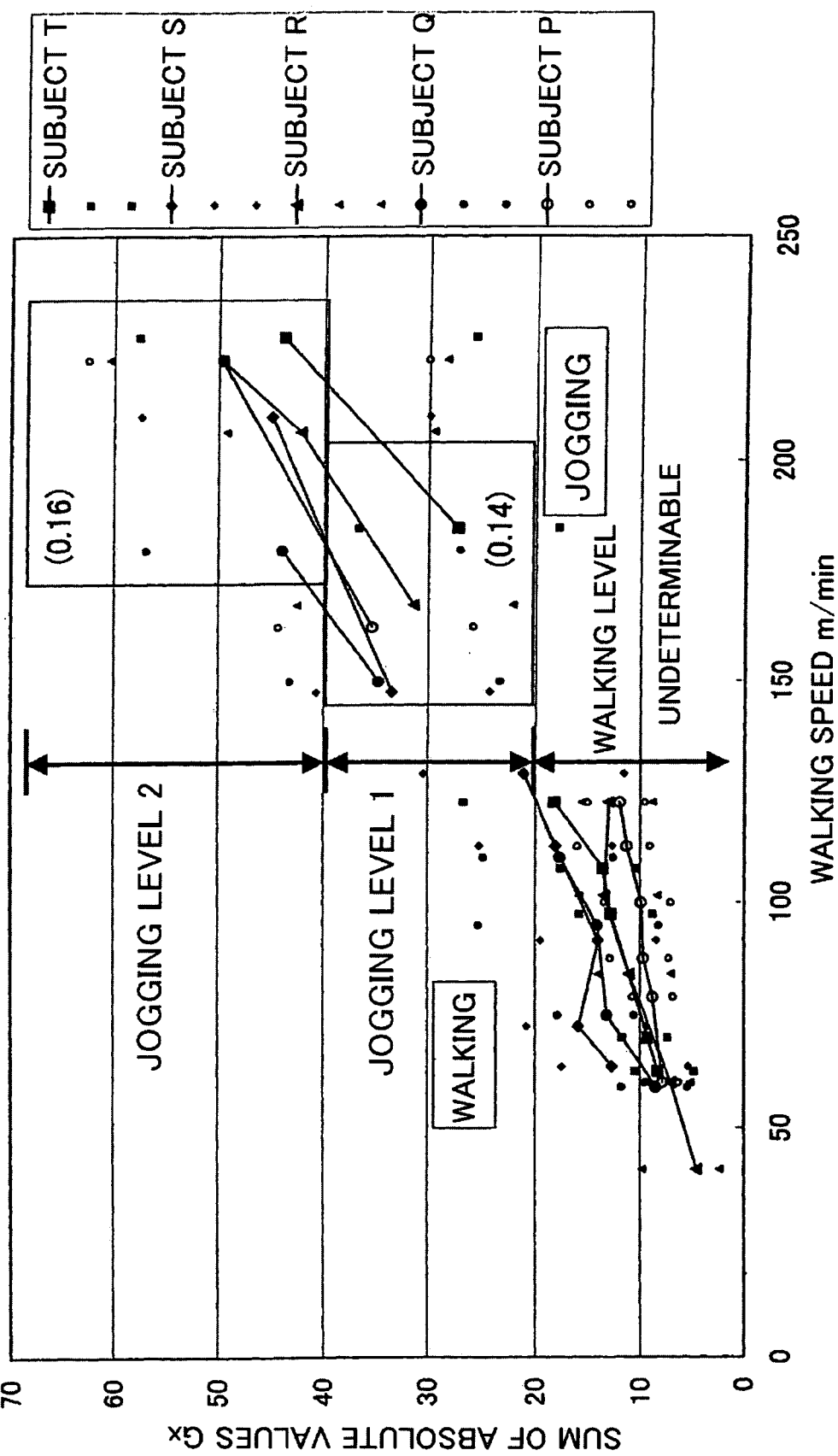
FIG. 8 is a graph showing a relationship between the walking and running speed and the sum of the absolute values of the acceleration Gx by the same subjects.

FIG. 8 is a graph showing a relationship between the walking and running speed and the sum of the absolute values of the acceleration Gx by the same five subjects. The running speed can be estimated from the acceleration Gx.

Figure 9:
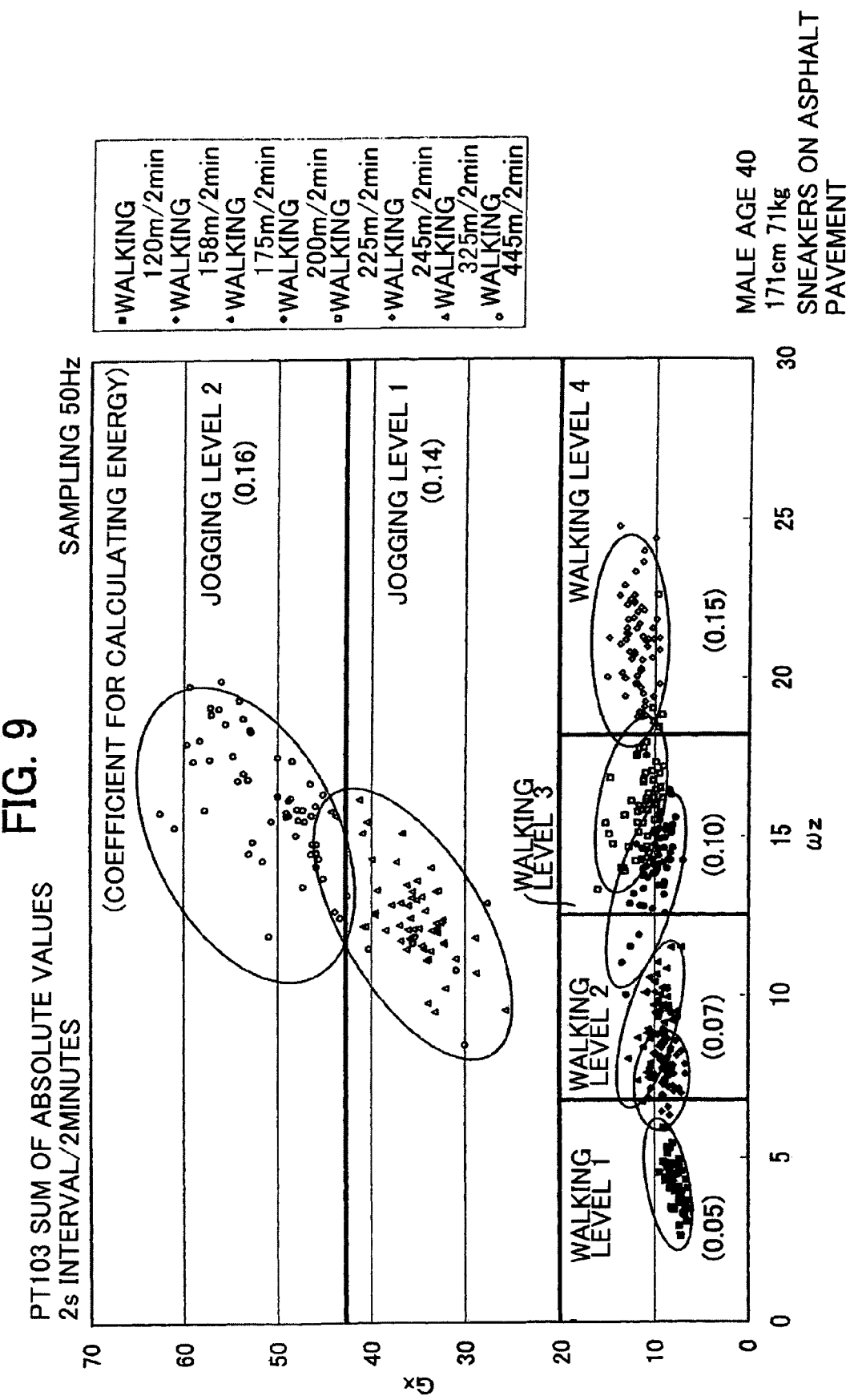
FIG. 9 is a graph showing distributions of sums of absolute values of acceleration Gx and angular velocity ωz, respectively, when the subject walks and runs at a designated speed.

FIG. 9 is a graph showing distributions of sums of absolute values of acceleration Gx and angular velocity ωz, respectively, when the subject P is made to walk and run at a designated speed. The data for the same speed are distributed within a certain area thereby showing that it is possible to sufficiently classify the walking by the level of acceleration Gx, and the running by the level of acceleration Gx and the magnitude of angular velocity ωz.

Figure 10:
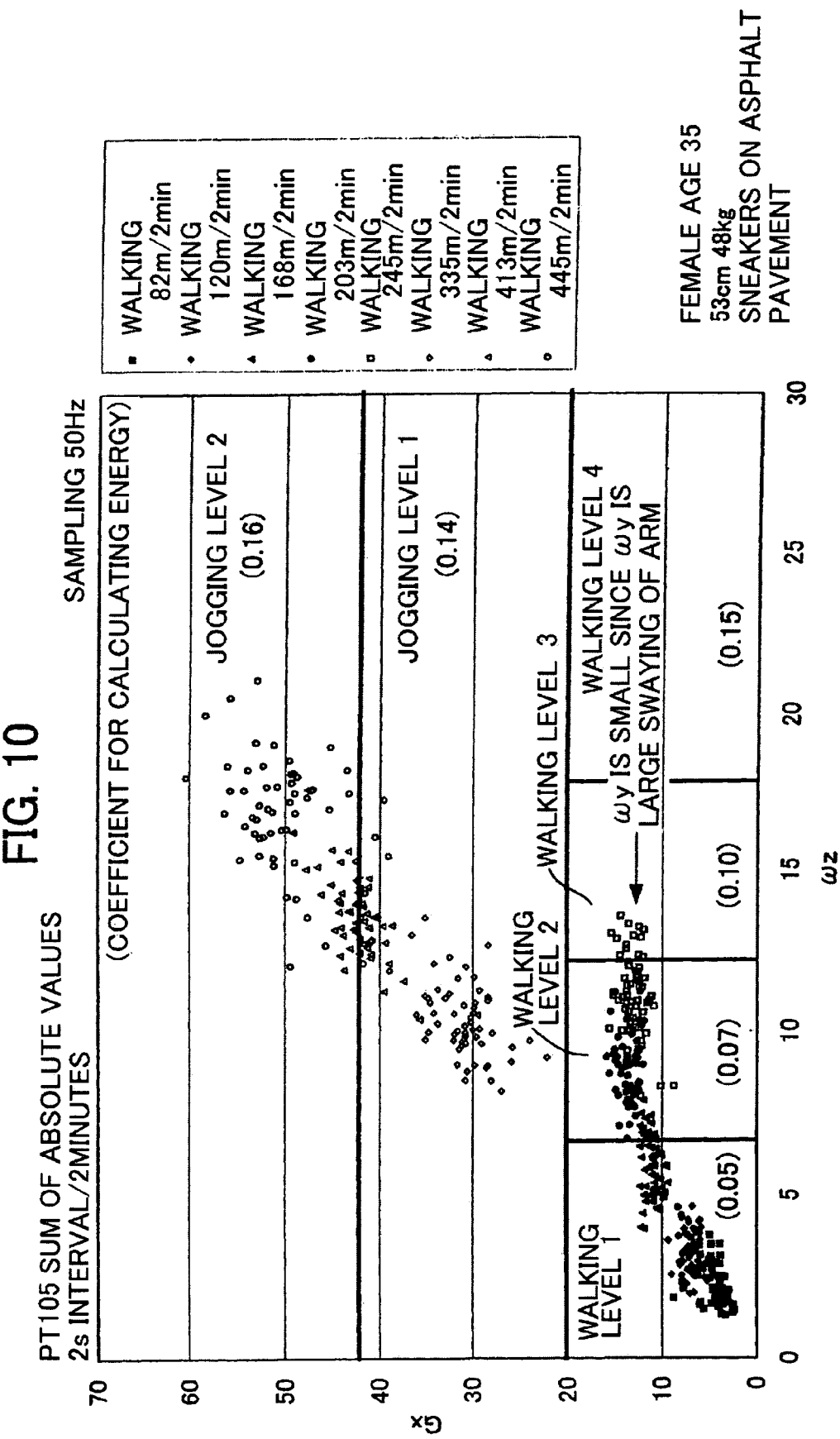
FIG. 10 is a graph showing similar data collected from a second subject.

FIG. 10 is a graph showing similar data collected with regard to the subject R. Here, the angular velocities ωz are distributed within a limited area, so that the walking speeds are not successfully classified. Observing the movements of the subject R, it was found that the subject had a habit of turning the palm toward the front, causing the orientation of the sensor of the device worn on the wrist to change, so that the accurate angular velocity ωz was not measured. One of the countermeasures to be taken is to slightly shift the movement measuring device about the wrist so that the data are corrected. On the other hand, no deficiency in classifying the running speed by the acceleration Gx was observed.

Figure 11:
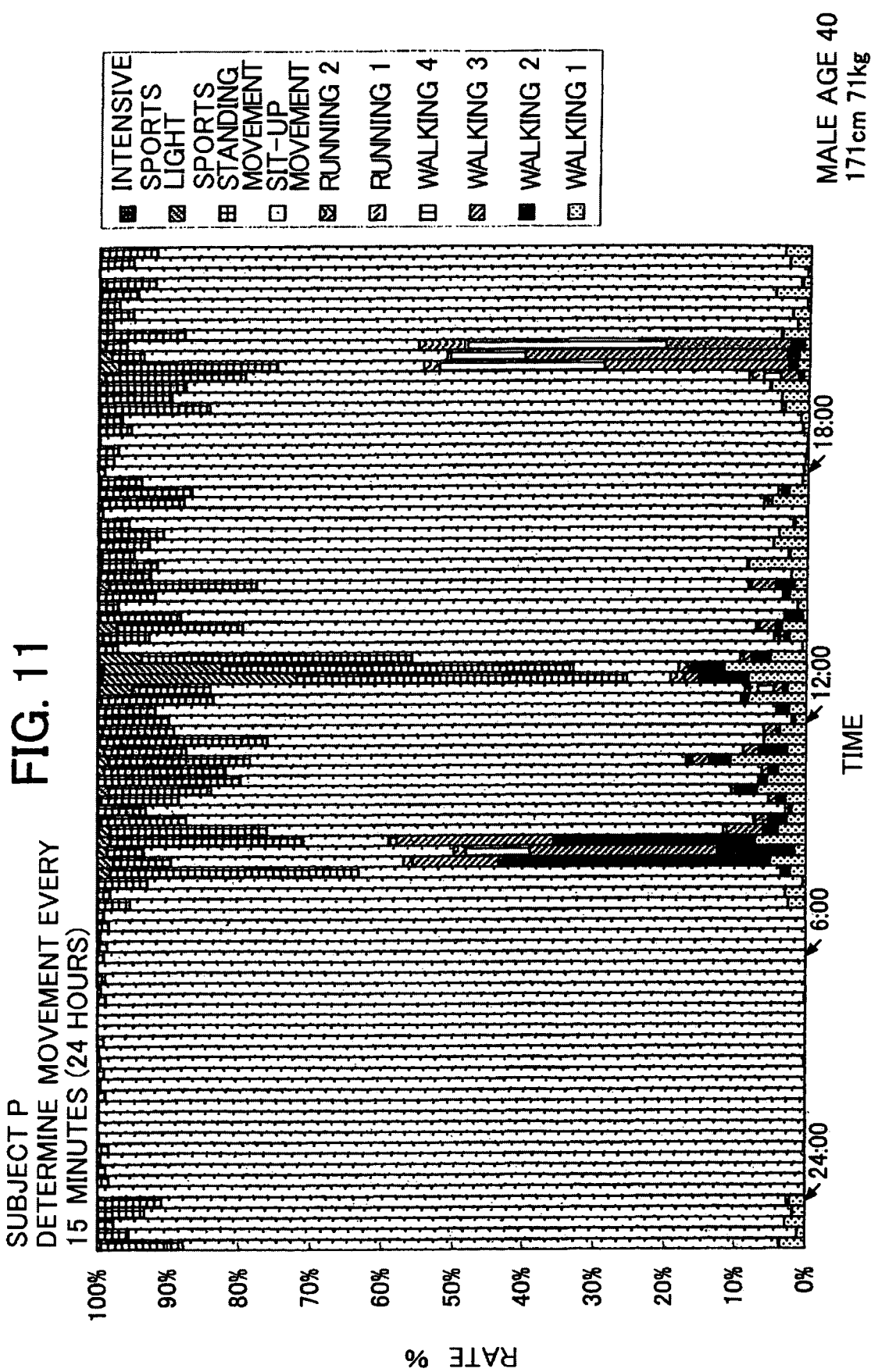
FIG. 11 is a graph showing a result when the movements of the first subject during one day is determined every fifteen minutes.

FIG. 11 is a graph showing the result when the movements of the subject P during one day is determined every fifteen minutes. It can be seen that the movement of the user can be analyzed by the present invention and therefore very useful.

Figure 12:
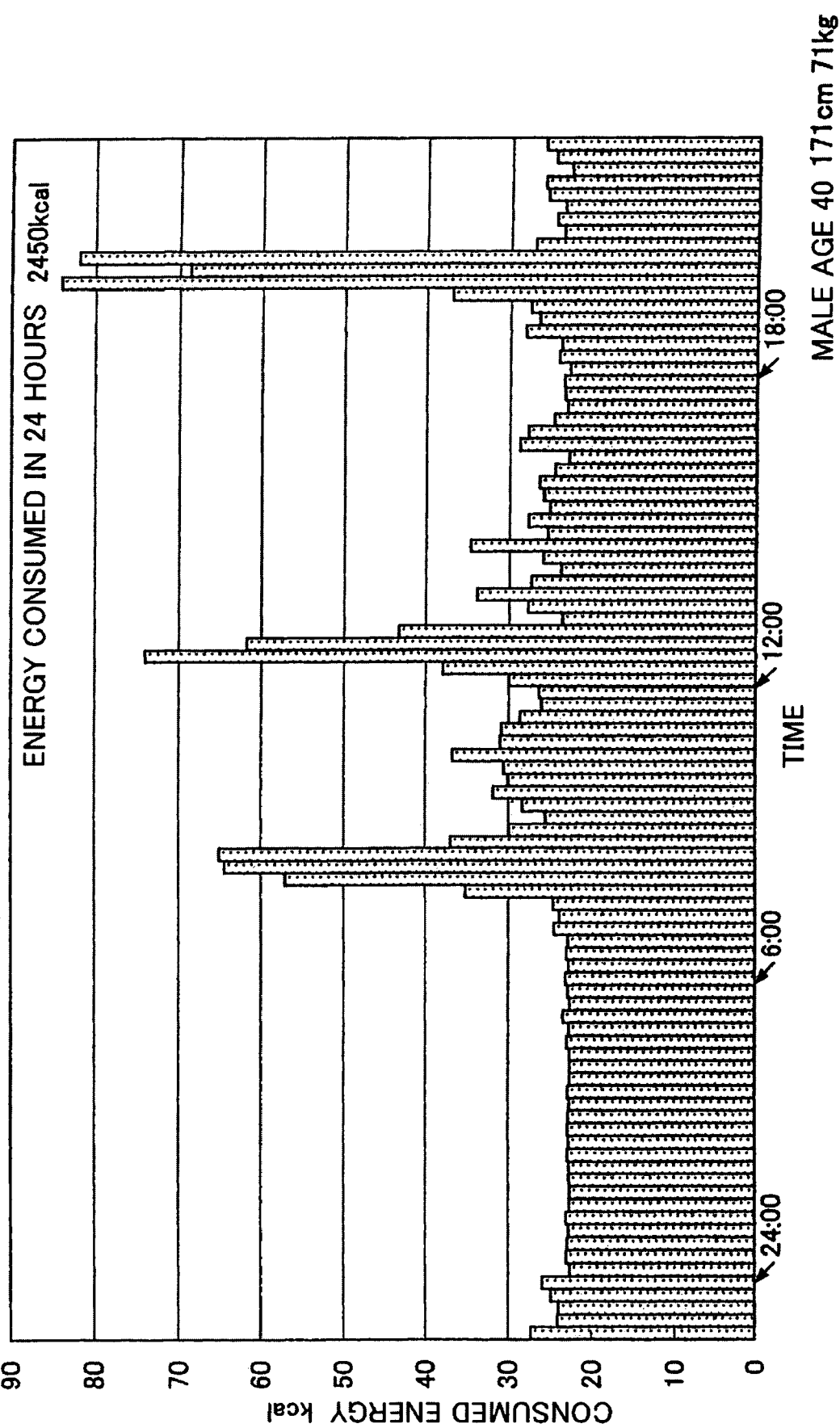
FIG. 12 is a graph showing variation in energy consumption on fifteen minute basis during one day.

FIG. 12 is a graph showing variation in energy consumption during one day on fifteen minute basis. The graph also shows that the invention is useful in understanding the pattern of energy consumption and total consumed energy of the user.

Figure 13:
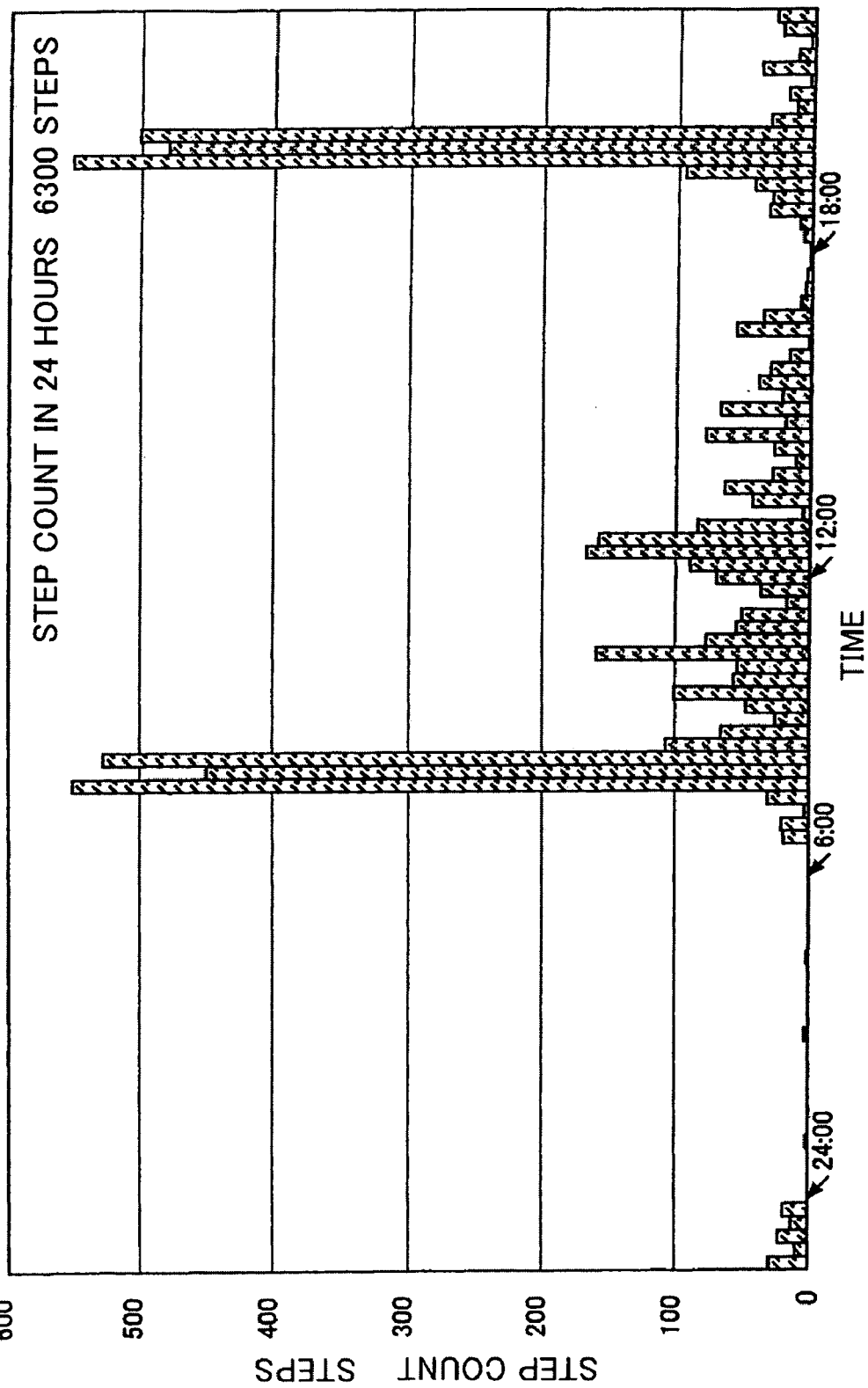
FIG. 13 is a graph showing the variation in step count on fifteen minute basis during one day.

FIG. 13 is a graph showing the variation in step count during one day on a fifteen-minute basis. The graph can be used for understanding the pattern of movements of the user and with the other graphs and data, become a reference material at a medical check up and for improving lifestyle.

The embodiment of the present invention is not confined to the one described above. For example, although the detecting directions of the acceleration and the angular velocity are both in single direction in the above described embodiment, a biaxial or triaxial acceleration and angular velocity sensors may be provided, in which case there is an advantage of increasing the information for analyzing the movements. In addition, it becomes possible to calculate the maximum and minimum absolute values of the accelerations and angular velocities without depending on the attitude and orientation of the device. If the measuring direction of the device is deflected caused by the tendency of the user as in the case of the subject R in FIG. 19, the maximum angular velocity can be calculated based on the angular velocity components in two directions, for example.

The movement sensor of the movement measuring device can be worn on other places such as upper arm, breast, waist, and leg, besides the wrist. The measured values from these devices are used singularly, or with the values measured at the wrist, to obtain a more accurate movement analysis. For example, when the angular velocity sensor is worn on a leg, the analysis of the exercise on a bicycle is facilitated.

In addition, instead of constructing the device worn on the wrist to have all of the functions, a device provided with minimum functions limited to those related to sensors may be provided so that the device is made small in size and light in weight to decrease the burden exerted on the user. The functions of calculation and thereafter are divided between a device worn on the waist and a mobile telephone to display the analysis results and the data are transmitted to a host computer. In this way, a certain degree of consideration may be paid to a pacemaker user.

Besides the calculation function described above, the device may be provided with a special detection function to contribute to the safety of the user. For example, in the case where the acceleration and angular velocity is hardly detected within a certain period of time, or a detected at a unthinkably low frequency, it may be that the user has fainted. If the user falls down, the movement sensor temporarily produces an output of an abnormal waveform, such as that showing a shock. There may further be a case where the user severely beats or shakes the device as a sign calling for help in emergency. The movement measuring device may be adapted to detect a pattern peculiar to such a sign movement and at the same time, transmit an emergency signal by sound or wireless. For emitting a sound, a speaker provided in the device is used, and when using a wireless, a radio wave is transmitted to an external equipment, or a rescue signal is transmitted by way of a radio transmitting device such as a mobile phone which the user has. When the device detects an abnormal value in acceleration or angular velocity, the rescue signal producing function is carried out with priority in the regular processing routine shown in FIGS. 4a to 4c, for example.

Figure 14:
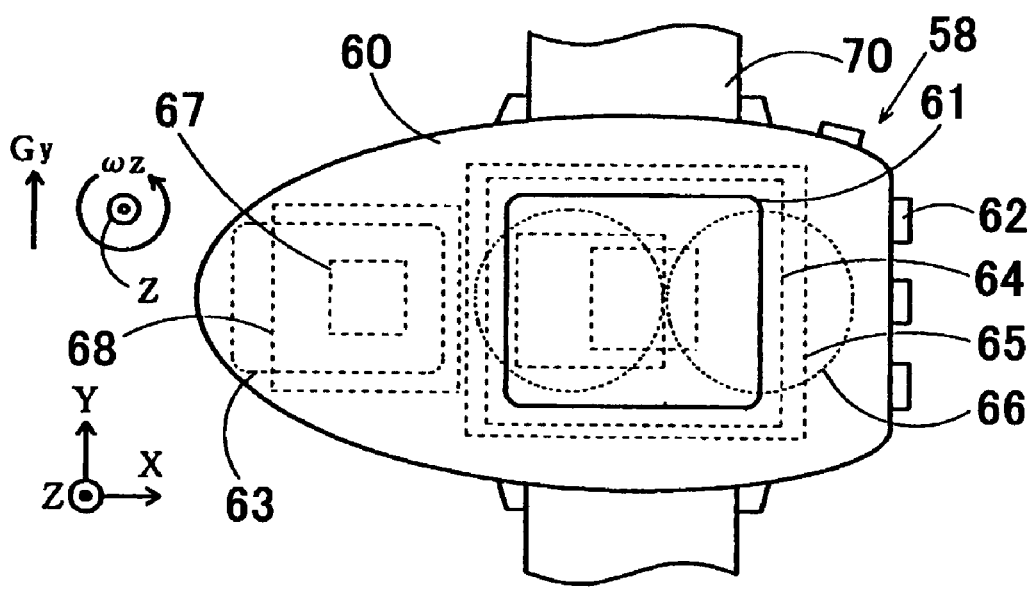
FIG. 14 is a plan view showing a movement measuring device of a second embodiment of the present invention.
Figure 15:
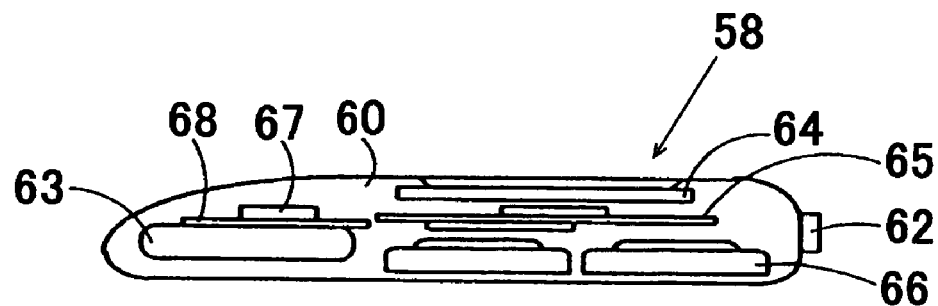
FIG. 15 is a sectional view taken along a center line thereof.

FIG. 14 is a plan view showing the movement measuring device of a second embodiment of the present invention, and FIG. 15 is a sectional view taken along a center line thereof. The present embodiment is adapted mainly to a device for transmitting an intension of a user to a third party.

Referring to FIG. 14, a case 60 of a movement measuring device 58 is provided with a display window 61 and a plurality of manipulating switches 62. In the case, there are provided a movement sensor 63, liquid crystal display 64, and a circuit board 65 on which an IC for a display driving circuit and a control circuit are mounted.

In addition, there are further provided power supply batteries 66, transmission module 67 having a transmitting and receiving IC, and a transmission substrate 68 on which the IC and an antenna of the transmission module 67 are mounted.

The case 60 is worn on a wrist with a band 70 wound around thereof. When a gesture or hand motion for a sign is made, information corresponding to the sign is shown on the display window 61, and at the same time, transmitted to an external device through a wireless. The movement sensor 63 is in a shape of a shallow box and is disposed in parallel to the display 64 and the circuit board 65.

In FIG. 14, the X, Y and Z coordinate systems are set as shown. References G and ω represent the magnitudes of the acceleration and angular velocity, respectively, and Gy and ωz show the directional components thereof, respectively.

Figure 16:
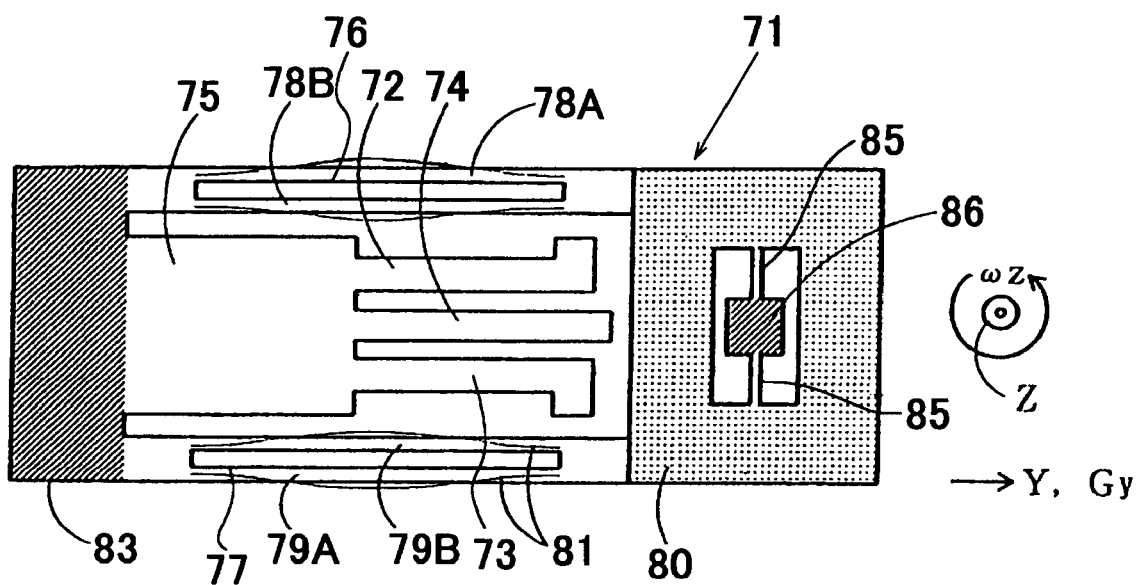
FIG. 16 is a plan view showing a movement sensor of the second embodiment.
Figure 17:
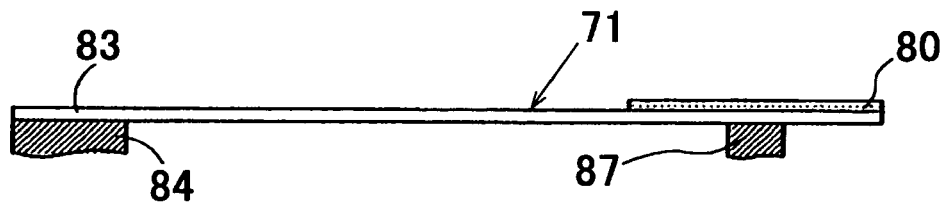
FIG. 17 is a sectional view thereof.

FIG. 16 is a plan view showing an inner main portion of the movement sensor 63 in the second embodiment, and FIG. 17 is a sectional view thereof. Although substantially the same as in the first embodiment, the description of the construction of the sensor will be repeated. A sensor vibrator 71 is cut out of a plate of a piezoelectric material such as a crystal Z plate where an angular velocity sensor, namely, the so-called vibration gyroscope, and an acceleration sensor are integrally formed, and housed in a air-tight container. The angular velocity detector is a three-pronged tuning fork comprising a pair of outer prongs 72 and 73 each adapted to vibrate in an open and close direction, a middle prong 74 which is not driven, and a fork base 75 connecting the prongs. The three-pronged tuning fork is a gyrosensor preferable for detecting the angular velocity ωz about the Z-axis perpendicular to the surface of the plate. Thus, the rotation causes Coriolis force to be generated at each of the outer prongs 72 and 73 and which are in the opposite direction to each other in Y-direction, and the couple of the Coriolis forces renders the middle prong 74 to vibrate. By synchronously detecting a vibration voltage at a detecting electrode of the middle prong, the Coriolis force, and hence an analogous output in proportion to the angular velocity ωz can be obtained.

The acceleration detecting portion of the sensor vibrator 71 comprises two pairs of vibrating rods 78A, 78B, 79A, 79B, formed in a pair of openings 76 and 77, interposing the three-pronged tuning fork, and an additional mass element 80 connected thereto. Each pair of vibration rods vibrate in symmetry in an open and close direction as shown by a vibrating posture 81. When an acceleration Gy in the Y-direction perpendicular to the arm of the user is exerted, there is generated an inertia on a loading mass which is a sum of the mass of the additional mass element 80 and that of the piezoelectric material directly underneath the mass element. The inertia applies a tension or a compression to each vibration rods, thereby affecting the natural frequencies thereof. The changes in the natural frequencies are directly or indirectly calculated by an arbitrary method, so that the acceleration Gy is obtained. The vibration rods may be provided singularly on each side of the sensor vibrator 71 as in the first embodiment so as to be vibrated symmetrically.

An underside of a base 83 of the sensor vibrator 71 is adhered to an upper surface of a pedestal 84 which is attached on a bottom of the container. The additional mass element 80 has a fixing portion 86 having a small area is mounted by way of a pair of supporting springs 85 on an upper surface of a pedestal 87 attached on the bottom of the container so that the sensor vibrator can be easily moved in the Y-direction but not in the undesirable X- and Z-directions.

Figure 18:
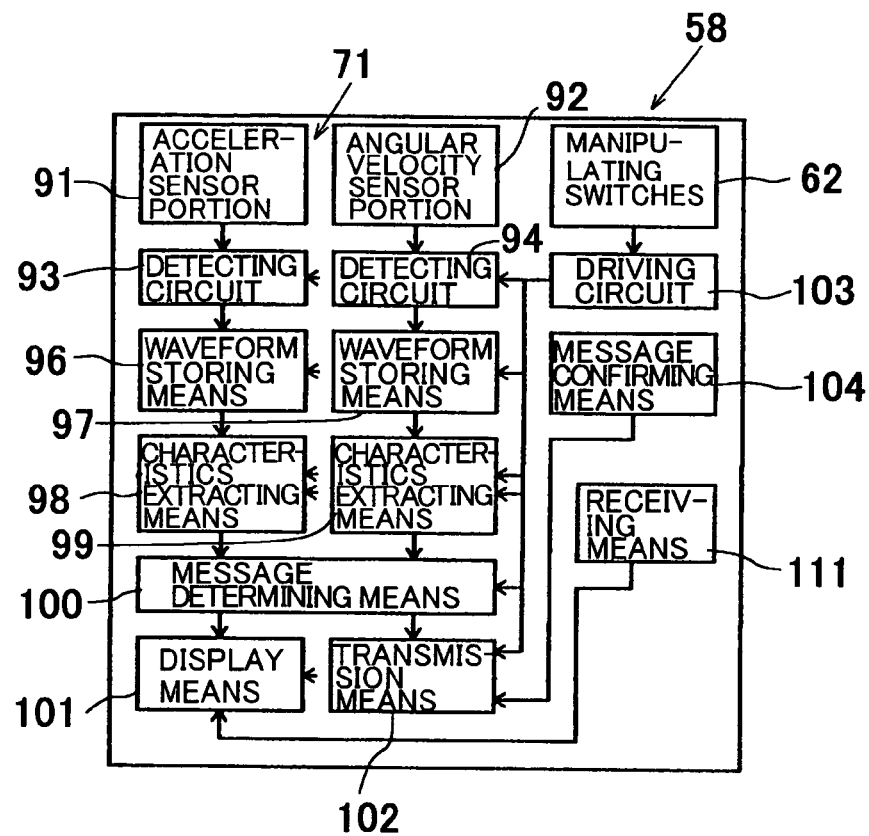
FIGS. 18 and 19 are block diagrams of a communication system of the second embodiment.
Figure 19:
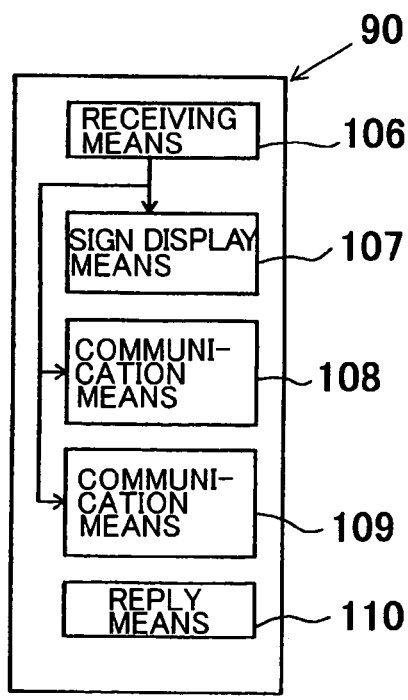

FIGS. 18 and 19 show block diagrams of a communication system using the second embodiment. The system comprises the movement measuring device 58 shown in FIG. 14 and a signal receiving device 90 provided at a receiving end.

The sensor vibrator 71 provided in the movement sensor 63 has an acceleration sensor portion 91 and an angular velocity sensor portion 92. The sensors and detecting circuits 93 and 94 operate so that the movement measuring device 58 produces an acceleration signal and an angular signal in time series.

When a user of the movement measuring device 58, for example, a handicapped person, presses the manipulating switch 62, a driving circuit 103 is operated. When the user makes a gesture, the acceleration signal and the angular velocity signal detected at the sensor portions 91, 92 and detecting circuits 93 and 94 are stored as waveforms at waveform storing means 96, 97, respectively, for a predetermined period of time. Characteristics and the combined conditions of the signal waveforms are checked at characteristic extracting circuits 98 and 99. The detected characteristics are compared with basic patterns of signals at a message determining circuit 100 so that it is determined which sign the user has made, and a signal corresponding to the result is generated. The circuits 98, 99 and 100 constitute the core of a movement analyzing means (circuit). The generated signal comprises a display signal and a transmission signal, and the former is applied to a display means 101 so that the signal is converted into letters, marks or sound and displayed for the user to confirm by a confirming means 104. Meanwhile, the transmission signal is externally transmitted through a transmission means 102.

The message confirming means 104 prevents a sign which is unintentional or erroneously detected from being transmitted, so that the operation of the transmission means 102 without the user's confirmation and manipulation is inhibited.

The receiving device 90 has a signal receiving means 106 for receiving the sign signal from the movement measuring device 58. The sign signal is then shown on a sign display means 107. If a receiver is not in possession of the receiving device, a communication means 108 for transmitting the signal to a mobile telephone of the receiver and a communication means 109 for transmitting the signal to a personal computer of the receiver are also driven, thereby transmitting the message. When the receiver operates the device in reply to the message, the reply signal is transmitted through a reply means 110 to a receiving means 111 provided in the measuring device 58.

Figure 20:
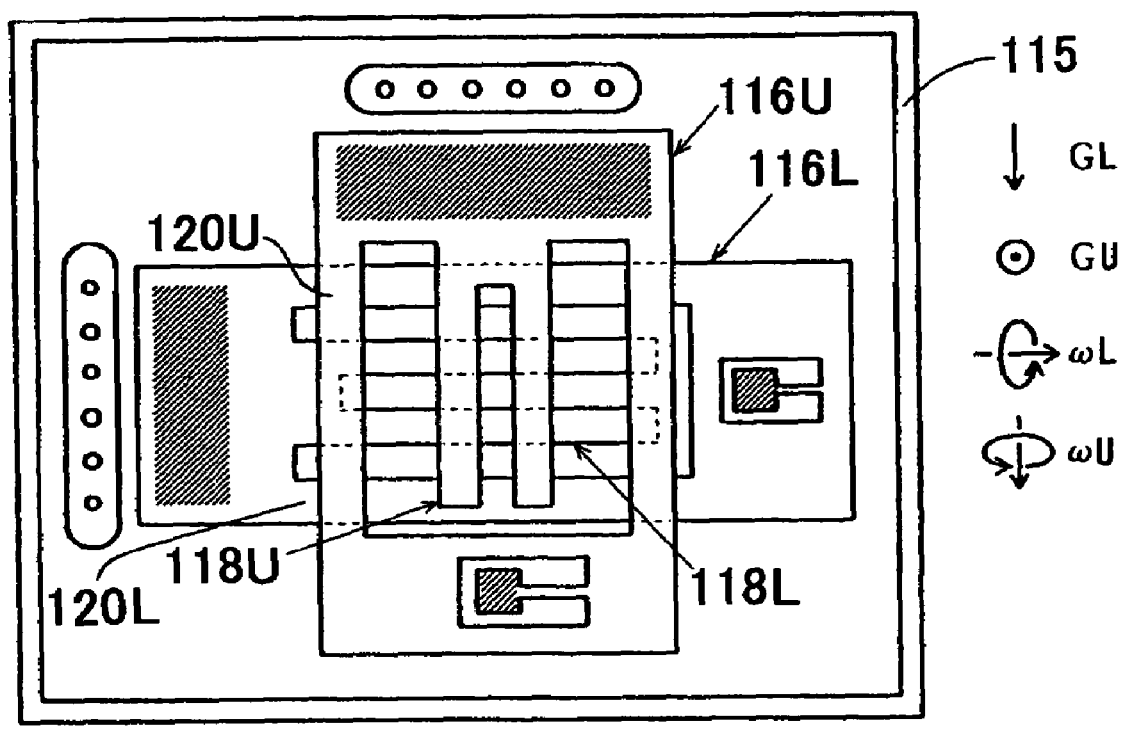
FIG. 20 is a plan view of another example of the movement sensor according to the present invention.

FIG. 20 is a plan view of another example of the movement sensor of the present invention. In the present example, two sensor vibrators, that is a lower sensor vibrator 116L and an upper sensor vibrator 116U, each having different detecting direction, are provided in a common container 115 formed in a shape of a box. The sensor vibrators are so disposed at the right angle of each other but in different vertical planes in order that the vibrators are not in contact with each other. Accordingly, angular velocities and accelerations in more than one directions can be simultaneously detected.

The lower sensor vibrator 116L comprises a two-pronged tuning fork 118L and vibrating rods 120L formed on the either side thereof, and the upper sensor vibrator 116U comprises a two-pronged tuning fork 118U and vibrating rods 120U formed on the either side thereof. Each of the two-pronged tuning forks is an angular velocity sensor portion and differs from that of the three-pronged tuning fork of the previous example in that the angular velocity thereof is obtained by detecting vibrations in a perpendicular direction of the planer surfaces of the prongs caused by the Coriolis force generated by the rotation about a rotating axis which is in parallel to the fork.

Each of the vibrating rods 120L and 120U is an acceleration detecting portion which is not vibrated. A quantity of a piezoelectric displacement caused by a static deflection of each vibrating rod, which corresponds to the acceleration, is simply directly measured. More particularly, the sensor vibrator 116L measures elastic deflection of the vibrating rods which is represented by a displacement within a planar surface of the additional mass element thereof perpendicular to an axis of the tuning fork, thereby obtaining an acceleration GL. On the other hand, the sensor vibrator 116U measures elastic deflection perpendicular to a planar surface of the vibrating rods which is represented by a displacement perpendicular to a planar surface of the additional mass element thereof, thereby obtaining an acceleration GU. If the sensor of FIG. 20 is singularly used, the container 115 is so disposed in the housing 60 that the accelerations GL, GU, angular velocities ωL, ωU are oriented in predetermined directions. When the sensor vibrator is additionally mounted over the sensor vibrator shown in FIG. 16 in the same direction as shown in the figure, the accelerations GL, GU, angular velocities ωL, ωU become accelerations Gx, Gz, angular velocities ωy, ωx, respectively. Thus, a sensor capable of arbitrarily detecting movements in every direction can be housed in a compact container.

Basic movements which can be easily directly detected in the case where the movements in all directions are detected by jointly using the sensors of FIGS. 16 and 20, for example, are listed below as the detecting directions.

Figure 21:
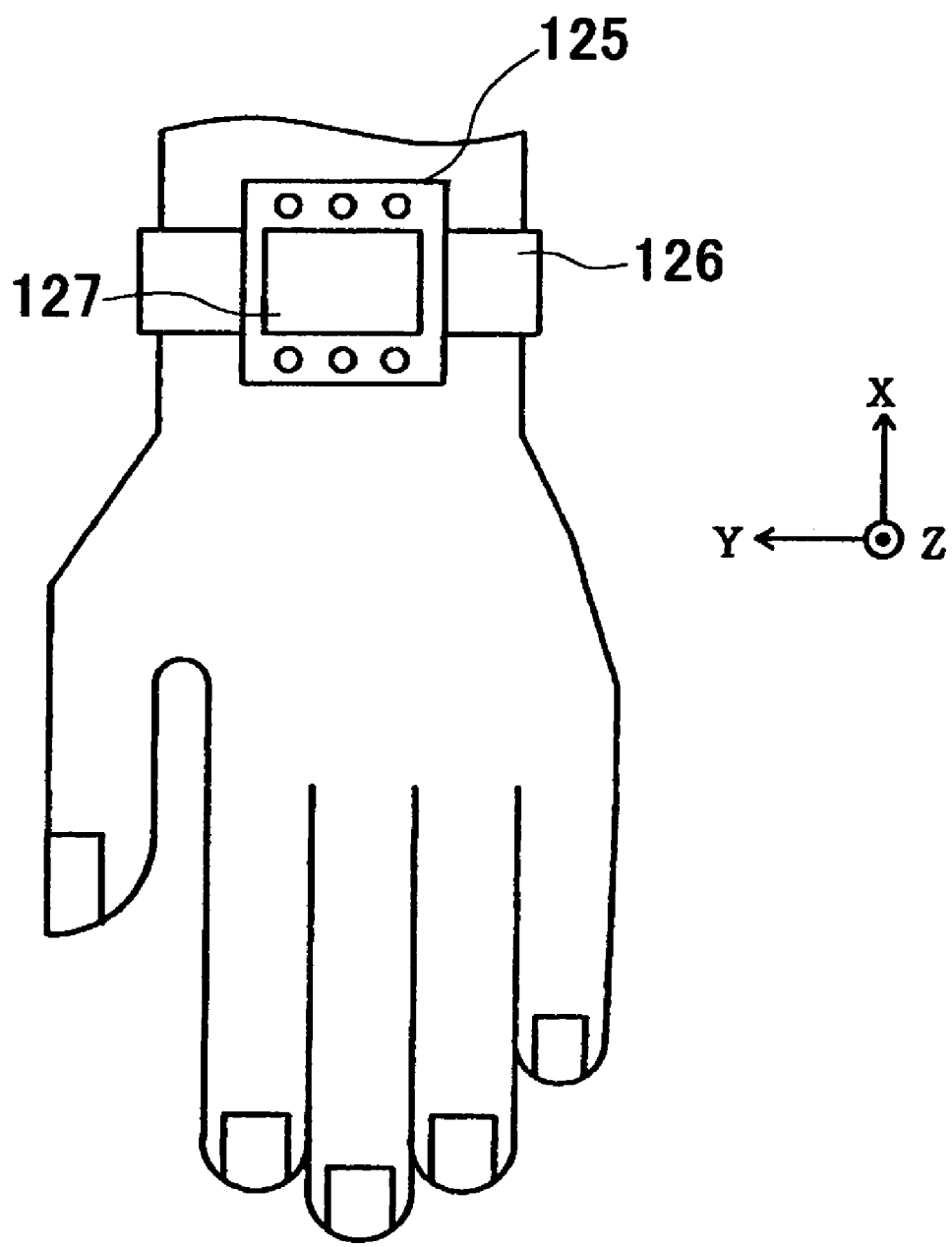
FIG. 21 is a schematic illustration of a third embodiment of the present invention.

(1) Cωx: twisting the lower arm about a wrist
(2) Cωy: waving the lower arm perpendicularly of the back of the hand as when beckoning a person
(3) Cωz: waving the lower arm in parallel to the back of the hand as in negation
(4) Gx: moving the lower arm back and forth in the direction thereof as when thrusting the arm forward
(5) Gy: moving the lower arm horizontally like a knife
(6) Gz: moving the lower arm in parallel to the back of the hand as when clapping hands FIG. 21 is a schematic illustration of a third embodiment of the present invention. A case 125 has a band 126 and a display 127. Axes of a coordinate system of the case 125 showing the directions are also shown in the figure.

Figure 22A:
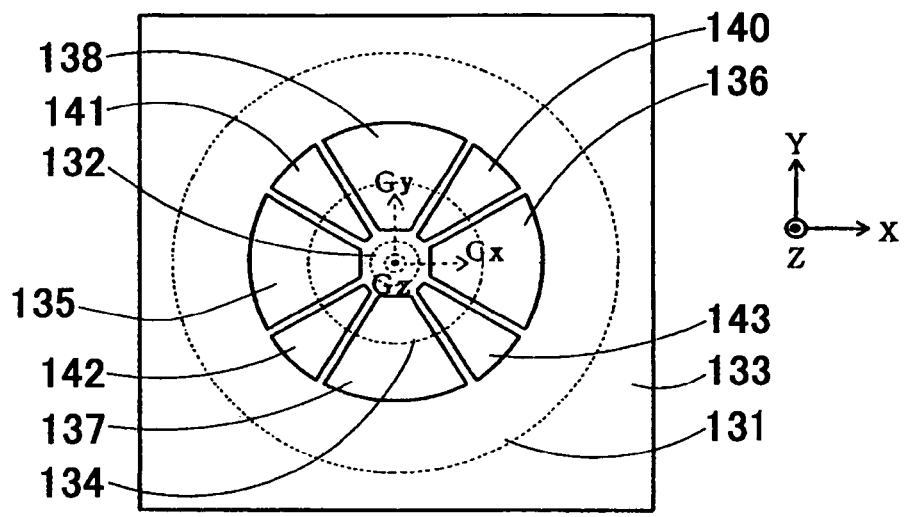
FIG. 22*a* is a plan view showing specific example of a triaxis acceleration sensor provided in the third embodiment.
Figure 22B:
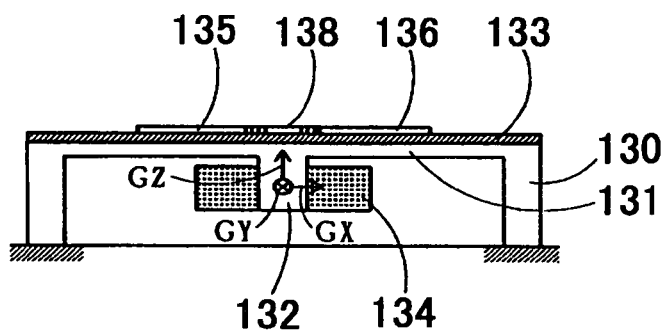
FIG. 22*b* is a sectional view thereof.

FIG. 22a is a plan view showing a specific example of a triaxis acceleration sensor provided in the third embodiment, and FIG. 22b is a sectional view thereof. The sensor of the present embodiment, for detecting three axes X, Y, and Z acceleration, is made of a machined phosphorus bronze block and has a supporter 130, metal disk 131 and a central shaft 132 mounted on the supporter, and a piezoelectric plate 133 secured on the circular plate. An annular mass loading element 134 is attached to the central shaft by force fit.

The piezoelectric plate 133 is made of a piezoelectric magnetic material such as lead zirconate titanate polarized in the direction of the thickness of the plate. On the upper surface of the plate, there are provided semicircular X-electrode films 135, 136, Y-electrode films 137, 138 and Z-electrode films 140, 141, 142, 143 each of which having an area approximately the half as those of other electrodes. The electrodes are formed by vapor deposition. The underside of piezoelectric plate 133 is adhered to the upper surface of the metal plate 131, the metal circular plate 131 serving as a common electrode of the piezoelectric plate 133. Each of the electrode films 135 to 143 and the metal circular plate 131 is connected to an acceleration detecting circuit.

Figure 23A:
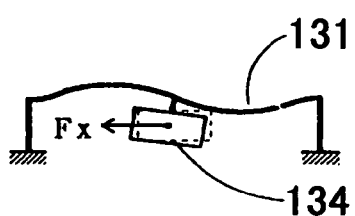
FIGS. 23*a* and 23*b* are schematic diagrams showing deformations caused by acceleration.
Figure 23B:
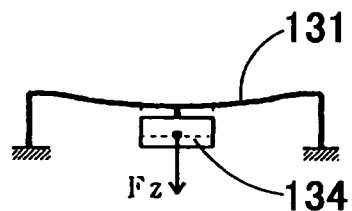

FIGS. 23a and 23b are schematic illustrations showing deformations caused by acceleration. The directions in the figures are the same as those of the sectional view. When an acceleration Gx is applied, an inertia Fx is exerted on the center of the gravity of the mass loading element 134 in the opposite direction, so that the mass loading element 134 is displaced in the direction of Fx, thereby deforming the metal circular plate 131 into an undulant form. The portion of the piezoelectric plate 133 adhered on the upper surface of the metal circular plate 131 and covered by the X-electrode film 135 is a projecting portion so that the portion expands. On the other hand, the piezoelectric material covered by the X-electrode film 136 is a caved portion so that the material contracts. Accordingly, there is generated a voltage proportional to the deflection of opposite polarity at each electrode film. In the case of Y-electrode films 137 and 138, since the deformations of the portions covered by the films are equally projected and caved, no voltage is generated. However, an acceleration Gy is also applied in parallel to the surface of the plate so that the similar phenomenon, although perpendicularly, occurs, so that the a voltage in opposite direction is generated at each of the Y-electrode films 137 and 138.

When an acceleration Gz is applied, an inertia Fz is exerted on the center of the gravity of the mass loading element 134 as shown in FIG. 23b, so that the metal circular plate 131 is deformed into a recess. Since the piezoelectric plate 133 is contracted equally at every portion, there are generated voltages equal in polarity and quantity at the Z-electrode films 140 to 143. The outputs of the X-electrode films 135 and 136 and Y-electrode films 137 and 138 are connected to respective inputs of differential amplifiers, and the outputs of the Z-electrode films are connected to inputs of an amplifier. By measuring the variation of theses outputs, the level of each component of the acceleration in various directions can be detected. Although the acceleration sensor in the present example is simple in construction, the acceleration in three axes can be detected.

Figure 24A:
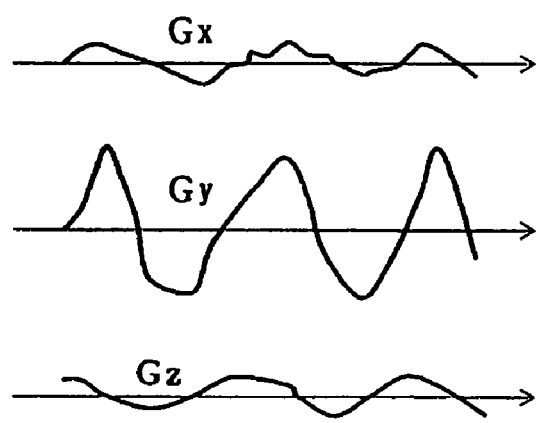
FIG. 24*a* shows examples of waveforms of detected accelerations Gx, Gy, and Gz in each axial direction during walking.
Figure 24B:
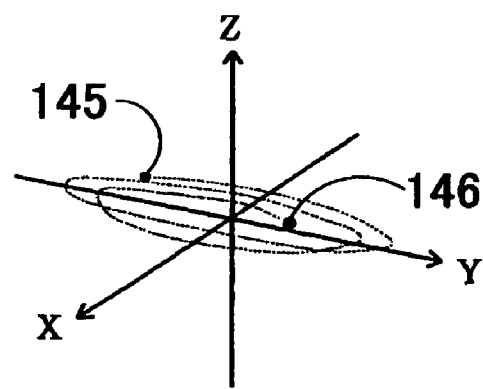
FIG. 24*b* is a perspective view of estimated loci re-synthesized on a three-dimensional coordinate system based on time to time location information of the sensor, dependent on a result after twice integrating each acceleration data.

FIG. 24a shows examples of waveforms of the accelerations Gx, Gy, and Gz in each axial direction during walking. The abscissa shows time and the ordinate shows detected voltage. The acceleration data in the form of digital data sampled at 50 Hz, for example, are stored for a predetermined period of time. FIG. 24b is a perspective view of estimated loci re-synthesized on a three-dimensional coordinate system based on time to time location information of the sensor dependent on a result after twice integrating each acceleration data when a wrist is reciprocated along the side of the body mainly in Y-direction as in walking. The reference 145 shows the starting point of measurement and the reference 146 shows the end point.

Figure 25:
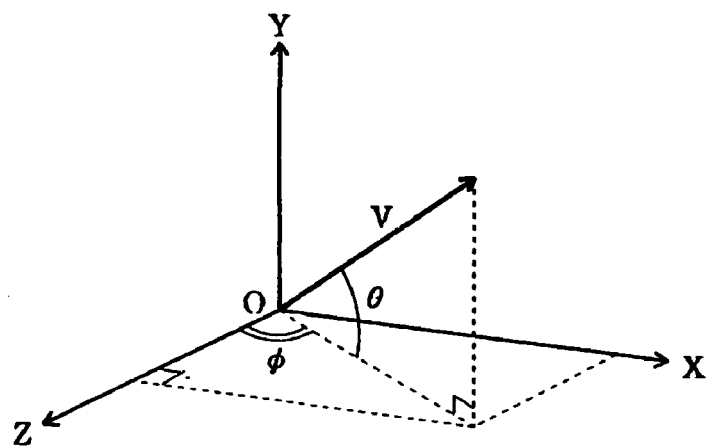
FIG. 25 is a perspective view for defining magnitude and azimuth of a positioning vector.

A movement analyzing circuit is provided for calculating a position vector and for determining the kind and strength of the movement. FIG. 25 is a perspective view for defining the magnitude and the azimuth of the positioning vector. The reference V designates a position vector at a point obtained from an acceleration integrated twice, the starting point of which is an average position of all of the position vectors within the integrating period (several seconds to several minutes). The starting point is designated as the origin. An end of the position vector indicates the magnitude of the displacement of the sensor and the azimuth thereof. The azimuth of displacement is shown as a inclination angle $\theta$ of the position vector V from the X-Z plane and an angle $\phi$ between a projection of the position vector V on the X-Z plane and the Z-ordinate, provided that the angles $\theta$ and $\phi$ are set as follows irrespective of the azimuth of the position vector V.

$$-90° < \theta \leq +90°$$

$$-180° < \phi \leq +180°$$

Values of various acceleration data are integrated to obtain various position vectors within a predetermined period so as to determine the movements of a user of the movement sensing module. First of all, an average of the magnitude of the various position vectors is related to, so to speak, an amplitude of the reciprocating-movement of the arm. Thus the average can be used not only to represent the intensity of the movement but also to differentiate the movements since the level of the value thereof varies in accordance with the type of the movement. Furthermore, an average direction (azimuth angles $\phi$ and $\theta$) of various position vectors can be deemed as inherent to a considerable degree in each type of movement. For example when comparing the movements of the arm waving in stretched state and in bent state, the direction of the movement of the sensor differs so that the direction of the position vector also differs.

Figure 26:
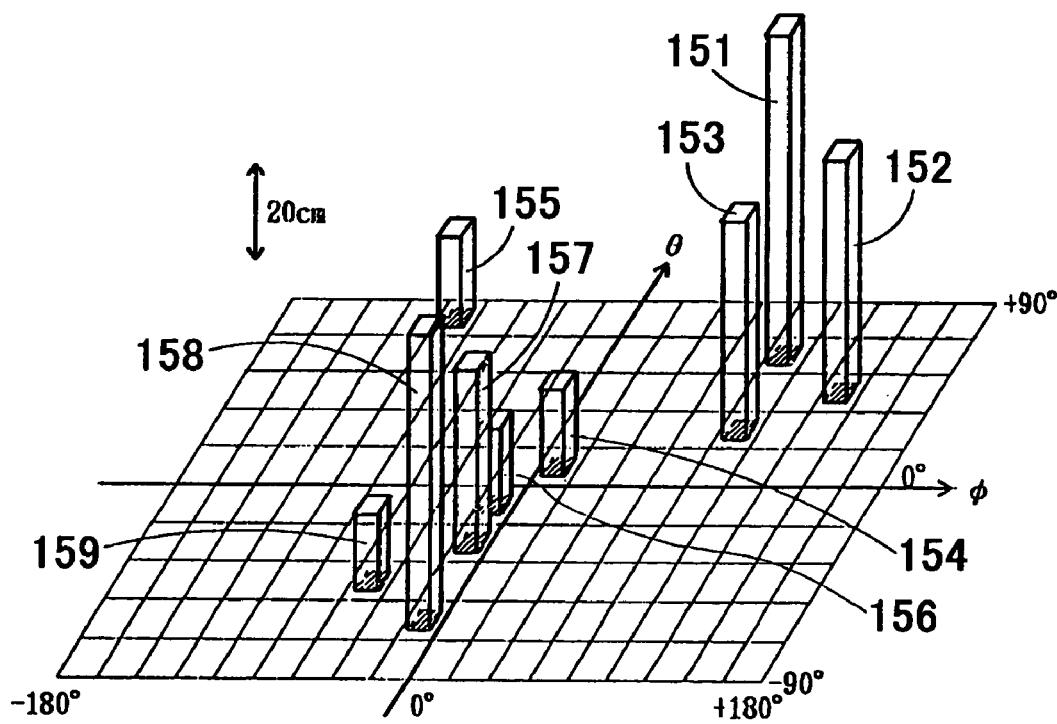
FIG. 26 shows a histogram of various movements determined in accordance with the present invention.

FIG. 26 shows a histogram of various movements determined in accordance with the present invention where an average magnitude and an average azimuth angle $\phi$ of the position vectors within a period where one type of movement is carried out is shown in a graph. On the basic plane, a $\phi$-ordinate and a $\theta$-ordinate are shown in perpendicular to each other, and averages of the magnitude of the position vectors are shown as the height of the graph. A male aged 40 was selected as the subject and was made to wear the movement sensing module having an acceleration sensor within on the left wrist and a pair of sneakers. The sampling rate was 50 Hz, and the A/D conversion accuracy was 10 bits.

A total of nine types of movements were carried out, covering both exercises of whole body and gesticulative movement involving only the arms. A bar 151 shows exercise walking, bar 152, running, bar 153, jogging, bar 154, clapping hands, bar 155, waving a hand, bar 156, slow walking, bar 157, normal walking, bar 158, rapid walking, and bar 159, walking with hands in pockets.

Regarding walking, the swing of the arm is increased as the walking speed increases, and the average angle θ is also increased, thereby increasing the Y-direction components. In exercise walking, running and jogging, the arms are bent compared to walking, so that the X-direction components are increased. The magnitude is greater in the exercise walking since the arms are consciously swayed. When hands are clapped, a large impulsive higher harmonic component is included in the acceleration information, so that in a common conventional method where movement pattern was directly extracted, the results are scattered thereby decreasing the determining accuracy. This is also true in the case of a method where the correlation between acceleration waveforms is applied. It has been found that a superior determining accuracy is achieved in the present invention.

It is obvious from FIG. 26 that the each of the movements has inherent magnitude and directivity, and despite the variety of the movements, the movements can be clearly distinguished from one another based on the characteristics of patterns with regard to magnitude and direction. Accordingly, it can be seen that, at least concerning a specific person, by comparing with his stored data, it is possible to determine the type of movement when a similar movement is executed. Furthermore, there is every possibility that the method of the present invention may be applied to a supplementary tool for facilitating communication such as by sign language.

The obtained average of the position vector data is not limited to the common arithmetic mean. As far as the object lies in improving the determining accuracy of various movements, the average may be geometric average, weighted average which involves some kind of weighting, harmonic average, or may use any other method used in general for obtaining an average after converting the data to a certain function such as adopting a median and processing the data after excluding abnormal values.

Figure 27:
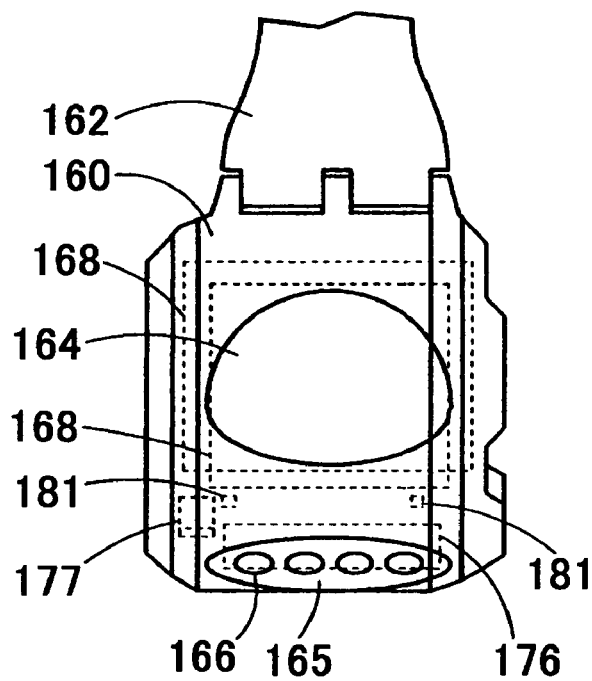
FIG. 27 is a plan view of a watch-shaped movement measuring device of a fourth embodiment.
Figure 28:
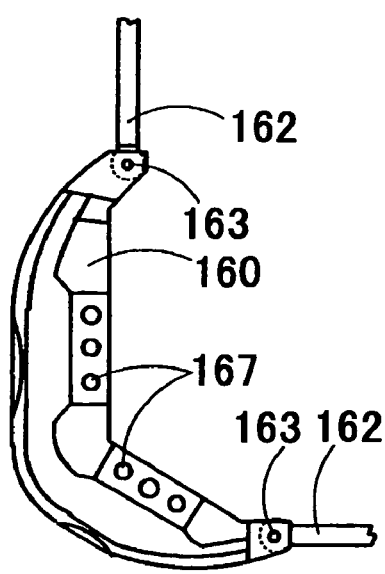
FIG. 28 is a right side view thereof.
Figure 29:
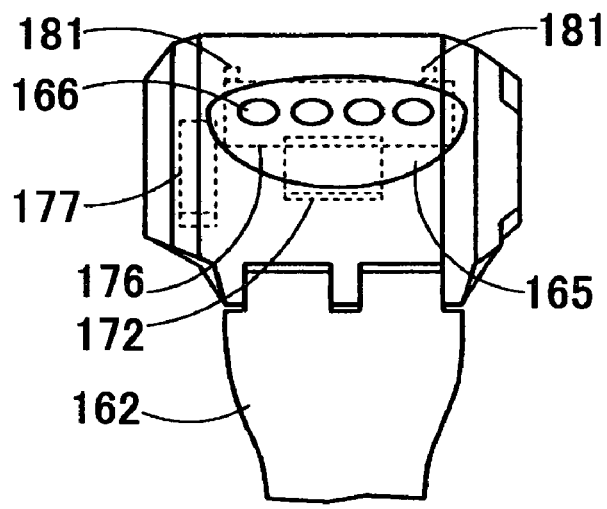
FIG. 29 is a view of a lower surface thereof as seen from the six o'clock direction.
Figure 30:
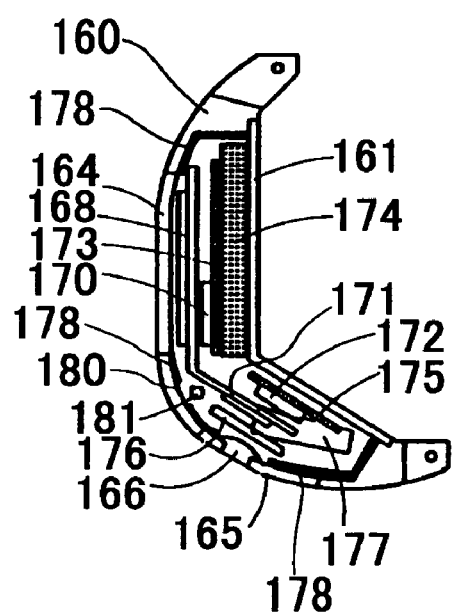
FIG. 30 is a sectional view thereof.

FIGS. 27 to 30 show a measuring device of a fourth embodiment according to the watch-shaped device of the present invention. FIG. 27 is a plan view, FIG. 28 is a right side view, FIG. 29 is a view of a lower surface as seen from the six o'clock direction, and FIG. 30 is a sectional view.

The measuring device comprises a case 160 and a back 161. The case is bent about 120° when seen from the sides thereof. Thus the case having therein a bulky mounting parts can be disposed on the wrist with a relatively small thickness, thereby enabling the device to be worn closely on the wrist and improving the wearability so as not to burden the user. Bands 162 to be wound on the wrist, which are flexible, are connected to the case 160 by way of band connecting pins 163.

A display window 164 for digitally indicating time and data is formed on the front face of the case 160 and an manipulating switch panel 165 is provided on the inclined lower surface thereof. Four manipulating switches 166 are disposed on the manipulating switch panel 154. The switches are used by the user for entering data such as number of steps, calorie and weight and for transmitting data to an external device. The switches 166 can be easily faced toward the wearer and so positioned and directed as to be easily operated by the fingers of the hand on which the device is not worn. On the right side surface of the case 160, there is provided six contact pins 167 for receiving and transmitting data and for charging a secondary battery which is the power source of the device.

At the inner side of a main surface, which is a plane parallel to the larger of the areas of the L-shaped case 160, there are provided, from the upper surface of the case toward the back, an LCD panel 168, acceleration panel 173 on which the LCD panel and an acceleration sensor portion 170 are mounted, and a battery 174. At the inner side of a sub-surface, which is a plane parallel to the smaller of the areas of the L-shaped case 160, there are provided a flexible substrate extending from the LCD panel 168, LCD driver 171 mounted on the flexible substrate, CPU 172 which includes a part or the whole of the movement analyzing means, a CPU board 175 on which the CPU is mounted, switch board 176 having a switch pattern of the manipulating switches 166, and an angular sensor portion 177.

The acceleration sensor portion 170 is a single axis sensor which detects an acceleration component in a three to nine o'clock direction of the watch-shaped device, namely, the direction of the wrist to arm.

The angular velocity sensor portion 177, which has a shape of an elongated rectangular box, is a single axis sensor adapted to detect angular velocity component about a rotational axis thereof and so disposed as to render the longitudinal side thereof substantially perpendicular to the main surface. The sensor 177 is inclined about 10° instead of being completely perpendicular because there are a few users who are inclined to swing their wrist outwardly instead of parallelly to the advancing direction when the arms are swayed when walking. Thus, the detecting rotational axis of such a user may be substantially approximate to the right and left axis of the body.

The case 160 is made of a transparent resin. On the underside of the case of the portion excluding the display window 164, an underside coating 178 is provided. The coating is preferably of a light reflecting material of silver metal or pearl white. Thus, not only is the inner portion of the sensor hidden but also the appearance is improved. A part of the underside coating 178 is left uncoated so as to form an uncoated portion 180 and a plurality of LED lamps 181 are disposed opposing the portion. When the LED lamps 181 are lighted, the light enters into the case 160 through the uncoated portion 180 and utilizing the transparent case 160 as a light transmitting member, are diffused about the case so that the watch-shaped device faintly glows in the dark.

Figure 31:
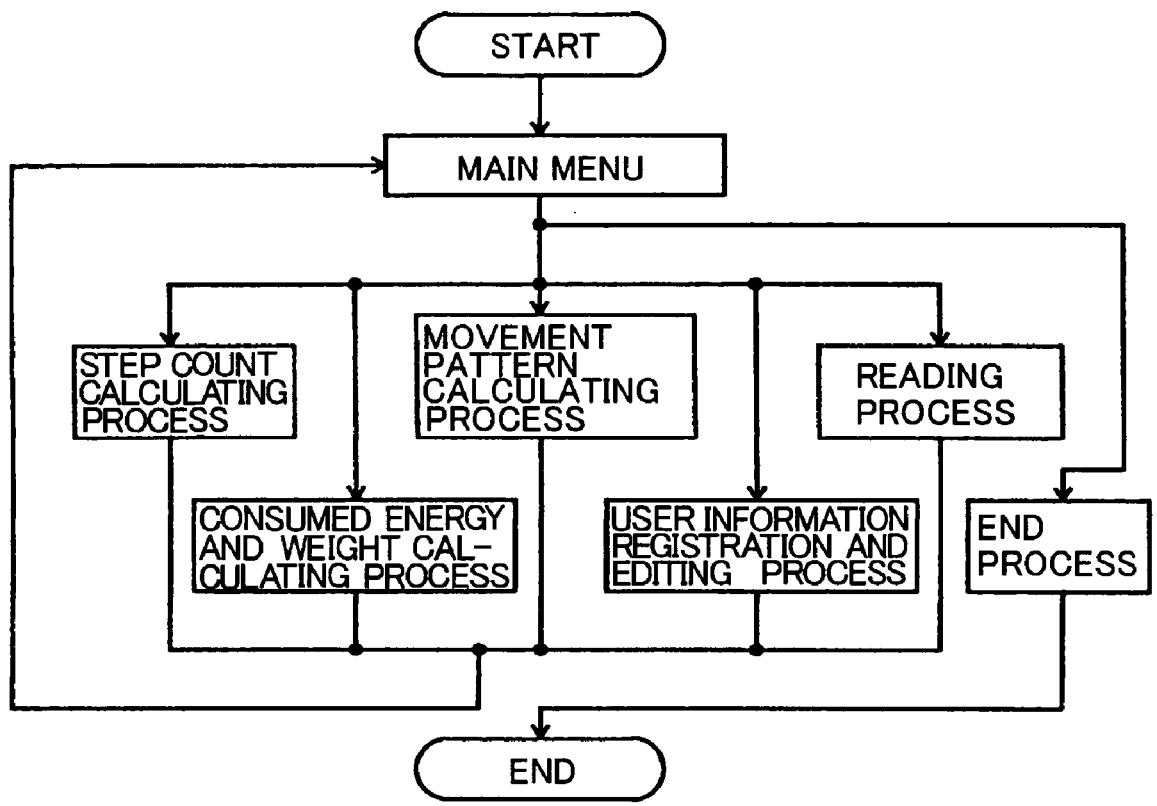
FIG. 31 is a flowchart for executing a functional operation in an external device.

FIG. 31 is a flowchart for executing a functional operation in an external device such as a notebook personal computer. The function of the device includes all or a part of the movement analyzing means and by operating a main menu, one of the functions are selected to execute the selected function from step count calculating process, consumed energy and weight calculating process, movement pattern calculating process, user information registration and editing process, and reading process. The program may return to the main menu from one function and proceed to another, or be ended when all of the functions are completed.

Figure 32:
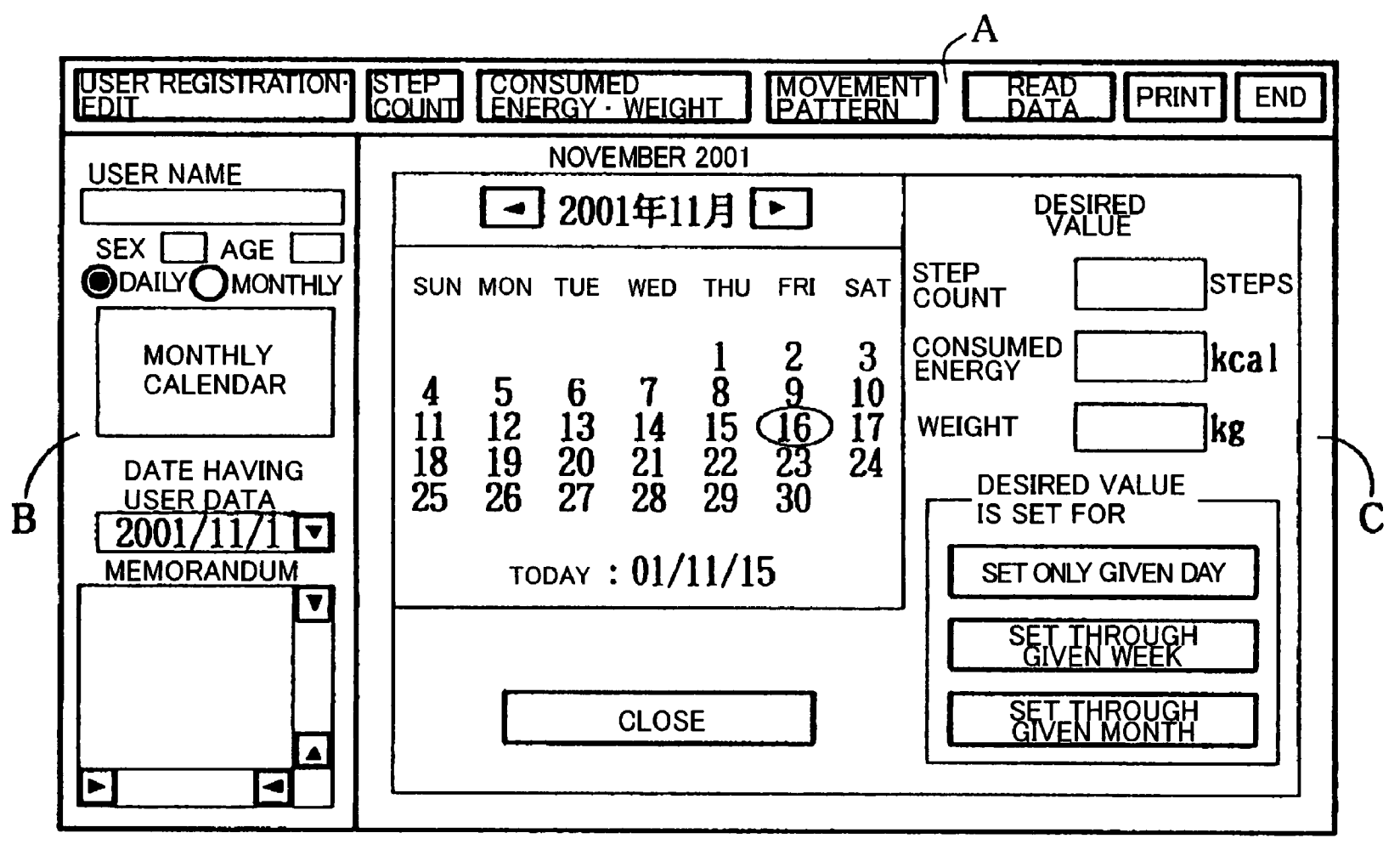

FIG. 32 shows a goal setting screen of the external device.

The display screen of the external device comprises a display area A, display area B and display area C. In the display area A at the top of the screen, there are disposed seven buttons for selecting various processes from the main menu or printing the screen. The left side display area B is provided for determining the user, for indicating days and months of which various calculation processes are carried out, and for recording a memorandum. The display area C is for indicating a screen on which is shown the results of various calculation processes and for setting conditions thereof as required. A calendar and operational buttons for setting the desired values, and the desired values are further shown in the area C.

Figure 33:
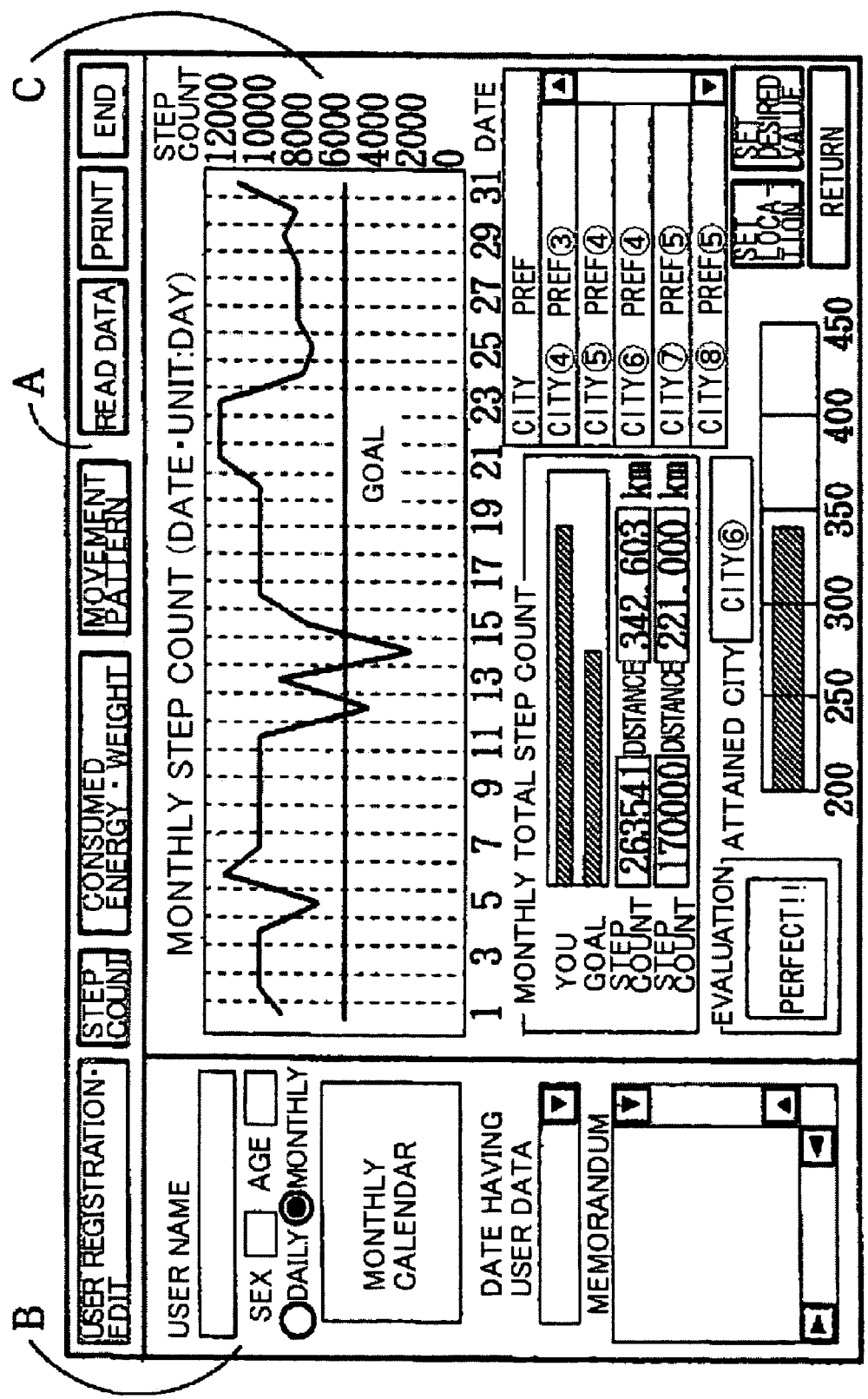
FIG. 33 is a step count processing screen of the external device.

FIG. 33 is a step count calculating process screen of the external device. In the display area C, there are indicated as well as related operational buttons, a graph showing the variation of the daily step count for one month as well as the desired value, total step count for the month and the desired value shown both in pictorial diagrams and numerical values, and the name of a city which the user has reached if the total step count is converted into a distance, evaluation comparing the attained result with the desired values and other information which enhances the motivation of the user.

FIG. 34 is an example of a setting screen for rendering the device to show the attained distance by a specific city names during the step count calculating process.

Functional operations when each of the processes is selected are described hereinafter. The past data are to be read out beforehand from the watch-shaped device and stored on a hard disk for example, as a text file.

Main Menu:
(1) Read user file from the text file and display the user at the completion of the last procedure.
(2) Select "DAILY" or "MONTHLY" and when the day or the month is selected from the calendar or a table, the data can be read from the text file in advance.
(3) The date of the data file provided in the personal computer regarding the user displayed on the screen can be selected.
(4) The "MEMODANDUM" can be used as a diary or for recording special remarks.
(5) If a "USER REGISTRATION AND EDIT" button is depressed, the program proceeds to a user registration and editing process.
(6) When "STEP COUNT" button is depressed, the program goes to a step count calculating process.
(7) When "CONSUMED ENERGY AND WEIGHT" button is depressed, the program goes to consumed energy and weight calculating process.
(8) When "MOVEMENT PATTERN" button is depressed, the program goes to movement pattern calculating process.
(9) When "READ DATA" button is depressed, the process for reading data from the watch-shape device is carried out.
(10) When "PRINT" button is depressed, output result (screen image) is printed.
(11) When "END" button is depressed, the application is terminated.

Step Count Calculating Process:
(1) Select calculating period. (one day or one month)
(2) The period is one day.
(A) When a date is selected, the following process is executed.
  (a) A text file of the subject date is read.
  (b) A graph showing a step count per 15 minutes is displayed dependent on the step count data.
  (c) Total step count and actual value and desired value of distance during the whole day is displayed.
  (d) The result of (c) is evaluated and displayed.
  (e) A pitch of the stride and speed per minute are calculated and displayed.
  (f) A pitch and speed per minute of a marathon runner are displayed as a comparison.
  (g) If a "SET DESIRED VALUE" button is depressed, the setting screen is shown.
  (h) If a "SET EVALUATING SUBJECT" button is depressed, a setting screen is shown.
  (i) If a time range is selected, and an "ENLARGE" button is depressed, the range of the abscissa changes, thereby enlarging the graph. The screen of the original time range can be retrieved with the operation of a button.
  (j) By operating a "RETURN" button, the step count calculating screen is closed.
(B) When the "SET DESIRED VALUE" button is depressed, the screen shown in FIG. 32 is shown.
  (a) An input screen is opened.
  (b) Select a date on the calendar and input a desired value.
  (c) In the case of "SET ONLY GIVEN DAY", register only for the selected date.
  (d) In the case of "SET THROUGH GIVEN WEEK", the same value is set for every day of the week.
  (e) In the case of "SET THROUGH GIVEN MONTH", the same value is set for every day of the month.
  (f) The screen is closed with the "CLOSE" button.
(C) Process when "SET EVALUATING SUBJECT" button is depressed
  (a) An input screen is opened.
  (b) Recorded data such as names of athletes, record time, distance, stride length, pitch, and speed per minute can be viewed by operating "FORWARD" and "REVERSE" buttons.
  (c) A "NEW" button is depressed for newly registering data.
  (d) New data can be registered with a "REGISTER" button.
  (e) Updated data can be written with an "ALTER" button.
  (f) Selected data can be deleted with a "DELETE" button.
  (g) The screen can be closed with an "END" button.
(3) When "MONTHLY" is selected, the screen shown in FIG. 33 is shown.
(A) When a month is selected, the following process is executed.
  (a) A text file of the entire subject month is read.
  (b) A graph showing actual and desired daily total step count are displayed dependent on the step count data.
  (c) Actual and desired values of total step count and distance during the whole month is displayed.
  (d) The result of (c) is evaluated and displayed.
  (e) The distance is calculated and compared with a distance from Tokyo to display the most approximate location.
  (f) When a "SET LOCATION" button is depressed, a location setting screen is shown.

(g) If a "SET DESIRED VALUE" button is depressed, the desired value setting screen is shown.
(h) By operating a "RETURN" button, screen is closed.
(B) When the "SET LOCATION" button is depressed, the following process is executed.
  (a) Open an input screen so as to show the screen in FIG. 34 on the display area C.
  (b) Recorded data can be viewed by operating "FORWARD" and "REVERSE" buttons.
  (c) A "NEW" button is depressed for newly registering data.
  (d) New data can be registered with a "REGISTER" button.
  (e) Updated data can be written with an "ALTER" button.
  (f) Selected data can be deleted with a "DELETE" button.
  (g) The screen can be closed with an "END" button.

Consumed Energy and Weight Calculation Process:
(1) Select calculating period.
(2) The following process is carried out.
(A) When the period is one day, the following process is carried out.
  (a) A text file of the subject date is read.
  (b) A graph showing consumed calorie per 15 minutes is displayed.
  (c) Actual values and desired values of total calorie and weight of the selected day are displayed.
  (d) The actual values are compared with the desired values and evaluated.
  (e) When the "SET DESIRED VALUE" button is depressed, a desired value setting screen is shown.
  (f) If a time range is selected, and an "ENLARGE" button is depressed, the range of the abscissa changes, thereby enlarging the graph. The screen of the original time range can be retrieved with the operation of a button.
  (g) By operating a "RETURN" button, the step count calculating screen is closed.
(B) When "MONTHLY" is selected, the following process is carried out.
  (a) A text file of the entire subject month is read.
  (b) A graph showing the following can be displayed.
    Actual daily values of the calorie and weight
    Actual daily value and desired daily value of the calorie
    Actual daily value and desired daily value of the weight
  (c) Actual and desired values of total calorie and the latest weight are displayed.
  (d) The actual values are compared with the desired values and evaluated.
  (e) If a "SET DESIRED VALUE" button is depressed, a desired value setting screen is opened.
  (f) By operating a "RETURN" button, the screen is closed.

Movement Pattern Calculation Process:
(1) Select calculating period.
(2) The following process is carried out.
(A) When the period is one day, the following process is carried out.
  (a) A text file of the subject date is read.
  (b) The ratio of each movement pattern is shown by a bar graph and a pie chart.
    In the bar graph, the bar representing one day is divided into sections, each of the sections showing a fifteen-minute period. The ratio can be indicated by coloring each pattern differently.
    In the pie chart, the pie is divided into four sections showing late night, morning, afternoon, and night, respectively. Alternatively, an hour may be arbitrarily selected and the ratio of the patterns per fifteen minutes may be shown by four pie charts.
  (c) The total daily movement patterns is shown by a pie chart. The ratio of roughly classified patterns is shown by a numeric figure.
  (d) When the "SET DESIRED VALUE" button is depressed, a desired value setting screen is shown.
(B) When "MONTHLY" is selected, the following process is carried out.
  (a) The daily ratio of each movement pattern is shown by a bar graph and a pie chart.
    In the bar graph, the bar is divided into sections, each section showing one day. The ratio can also be indicated.
    In the pie chart, total may be shown weekly or in accordance with each day of the week.
  (b) The total movement patterns of one month is shown by a pie chart. The ratio of roughly classified patterns is shown by a numeric figure.
  (c) By operating a "RETURN" button, the screen is closed.

Storing Process:
(1) Open a storing screen.
(2) Select the user of the data to be stored.
(3) Store data by depressing an "ENTER" button.
(4) Close the screen by depressing an "END" button.

Printing Process:
Print the current screen.

User Registration and Edit Process:
(a) Open an input screen.
(b) Registered data can be viewed by operating a "FORWARD" or "REVERSE" buttons.
(c) A "NEW" button is depressed for newly registering data.
(d) New data can be registered with a "REGISTER" button.
(e) Updated data can be written with an "ALTER" button.
(f) Selected data can be deleted with a "DELETE" button.
(g) The screen can be closed with an "END" button.

Other modifications besides the embodiment described above is explained hereinafter.

(1) The watch-shaped device is provided with a built-in wireless transmitter and the external device is provided with a receiver so that the user can make an arm waving gesture in emergency thereby transmitting a sign for rescue and help to a remote place.

(2) The angle of intersection between the main surface and the sub-surface is effective when in a range between 100° and 160°.

(3) Although substantive acceleration sensor and angular velocity sensors are used in the present embodiment, an integrated sensor such as that used in the first embodiment of the present invention can be used to provide a smaller movement measuring device. Furthermore, when a sensor having a detecting axis differing from those of the present embodiment is added, it will be possible to increase the number of detectable movement patterns and gesture signs.

(4) In order to render the intense light of the LED lamp which enters the case invisible from view, an outer surface of the light entering section of the case may be coated with a light-shielding material or a light-reducing material, or alternatively, the LED lamp may be disposed behind an opaque or a dark-colored member.

(5) The back may be a curved surface such as cylindrical surface in addition to the shape wherein two planes intersect.

(6) The movement measuring device may further be provided with pulse rate and blood pressure sensors so that information therefrom can be further used in combination with the detected movement information for a higher standard of health control.

A wrist watch-shaped physical movement measuring device of the fifth embodiment of the present invention will now be described. In the present embodiment, the analysis of movements as that in the first embodiment is carried out using acceleration data from a biaxial acceleration sensor without using the angular velocity sensor. Detected two data of acceleration are accelerations Gx and Gy in the X and Y directions, respectively, in FIGS. 1, 14 and 21. The acceleration Gx is applied in exactly the same manner as the acceleration Gx in FIGS. 4a and 4b. The acceleration Gy is integrated once with regard to time to obtain data which is approximate to that of a tangential velocity of a wrist motion substantially forming a circular path along the body and which can be substituted for an angular velocity ωz. The acceleration Gy is in a direction, although not accurately, but substantially equal to the tangential direction of a path of a swaying wrist. Since the center of the circular path must be somewhere between the shoulder and the elbow, the radius of the path of the wrist is within a certain range. Since the tangential velocity is a product of the radius of the path and angular velocity, there is a proportional relationship having a proportional constant relative to the build of the user between the acceleration Gy and angular velocity ωz. Thus it is clear that one can be substituted by the other in analyzing the movement. Should there be a need, the acceleration Gx may further be used for correction calculation. The integration is executed as one of the functions of the movement analyzing circuit means. In order to prevent an offset component, that is an integration error, from occurring in the integration, low frequency components in the input data and/or the output data, are removed by a filter or calculation. This is also a necessary consideration which should be taken when integrating twice in the third embodiment in order to prevent calculation error in the output regarding the location.

The acceleration sensor used in the fifth embodiment is the one shown in FIG. 22 for example. In the present embodiment, since it is not necessary to use the acceleration Gz, the Z-electrode films 140 to 143 are not connected, or altogether removed to increase each of the areas of the X-electrode films 135 and 136 and Y-electrode films 137 and 138. The advantage of the present embodiment lies in that the angular velocity sensor, which needs to be constantly vibrated, is obviated and only the acceleration sensor, which detects static deflection or force, is used. Thus, power for constantly exciting the sensor becomes unnecessary, thereby elongating the life of the power source battery, or miniaturizing the watch-shaped device as well as the battery. The biaxial acceleration sensor of the present embodiment may be substituted by two single axis acceleration sensors which need not be constantly excited.

PROBABILITY OF INDUSTRIAL EXPLOITATION

In accordance with the present invention, with the ingenuity of using a compact movement sensor and an L-shaped case, there is provided a movement measuring device which do not burden the user even when worn for a long time, and further facilitates the movement measurement, health control, and the transmission of gesture signs, thereby increasing the usability of the device.

The invention claimed is:

1. A physical movement analyzing device, comprising:
an acceleration sensor for measuring acceleration data on at least one axis;
an angular velocity sensor for measuring angular velocity data on at least one axis;
a graph having a system of coordinates formed by combining at least one acceleration (G) and at least one angular velocity (ω), in which measured acceleration data and measure angular velocity are to be recorded;
analyzing means for analyzing kinds of movements from a coordinate of data recorded in the graph; and
a display for displaying an analyzed movement.

2. The physical movement analyzing device according to claim 1 characterized in that the acceleration data in one direction are acceleration data in a direction from a wrist toward an elbow, and the angular velocity data in one direction are angular velocity data of a rotation of the wrist about the elbow.

3. The physical movement analyzing device according to claim 1 characterized in that the acceleration data in one direction is acceleration data in a direction from a wrist toward an elbow, an acceleration of rotation of the wrist about the elbow in tangential direction is detected to produce an acceleration signal, and the detected acceleration signal is once integrated to produce an acceleration data signal which is substituted for the angular velocity data in one direction.

4. The physical movement analyzing device according to claim 1 characterized in that the analyzing means classifies the movement into walking or running movement and other movements based on the magnitude of the acceleration data and a periodicity of at least one of the acceleration data.

5. The physical movement analyzing device according to claim 4 characterized in that the running movement is further classified into a plurality of intensity levels in accordance with the magnitude of the acceleration data, and the walking movement is further classified into a plurality of intensity levels in accordance with the magnitude of the angular velocity.

6. The physical movement analyzing device according to claim 1, further comprising a case, wherein the physical movement analyzing device is mounted in the case.

7. A physical movement analyzing device, comprising:
a case having a pair of bands for wearing on a wrist of a user, and having a display;
a plurality of acceleration sensor means provided in the case for measuring independent acceleration data on three axes;
a graph having a system of location coordinates formed by combining more than two axes;
converting means for converting the acceleration data to location data by integrating the acceleration data;
movement analyzing means for recording the location data on the graph, and for analyzing the recorded location data to distinguish physical movements; and
displaying means for displaying distinguished movement on the display of the case.

8. The physical movement analyzing device according to claim 7 characterized in that the three axes comprises a first direction which is substantially parallel to a back of a hand, and substantially parallel to the bands, a direction substantially perpendicular to the back of the hand, and a direction substantially directed from a wrist to an elbow.

9. The physical movement analyzing device according to claim 7 characterized in that the movement analyzing means classifies the movement into walking or running movement and other movements based on the magnitude of the acceleration data in three axes and a periodicity of the data in at least one of the axes.

10. The physical movement analyzing device according to claim 7 characterized in that the converting means integrates twice the acceleration data.

* * * * *